US009358415B2

(12) United States Patent
Champion

(10) Patent No.: US 9,358,415 B2
(45) Date of Patent: Jun. 7, 2016

(54) SPINAL THERAPY DEVICE

(71) Applicant: Andrew Oakford Champion, Peoria, IL (US)

(72) Inventor: Andrew Oakford Champion, Peoria, IL (US)

( * ) Notice: Subject to any disclaimer, the term of this patent is extended or adjusted under 35 U.S.C. 154(b) by 201 days.

(21) Appl. No.: 14/154,738

(22) Filed: Jan. 14, 2014

(65) Prior Publication Data

US 2014/0200498 A1 Jul. 17, 2014

Related U.S. Application Data

(60) Provisional application No. 61/752,699, filed on Jan. 15, 2013.

(51) Int. Cl.
*A61F 5/00* (2006.01)
*A63B 21/00* (2006.01)
(Continued)

(52) U.S. Cl.
CPC ........ *A63B 21/00043* (2013.01); *A61H 1/0292* (2013.01); *A63B 21/0023* (2013.01); *A63B 21/00185* (2013.01); *A63B 21/0442* (2013.01); *A63B 21/0557* (2013.01); *A63B 21/068* (2013.01); *A63B 21/1419* (2013.01); *A63B 21/1449* (2013.01); *A63B 21/1469* (2013.01); *A63B 21/1484* (2013.01); *A63B 21/15* (2013.01); *A63B 21/151* (2013.01); *A63B 21/152* (2013.01); *A63B 21/153* (2013.01); *A63B 21/1663* (2013.01);
(Continued)

(58) Field of Classification Search
CPC ............... A61B 17/42; A61B 19/5202; A61B 2017/00017; A61B 2017/00115; A61B 2560/0412; A61B 2562/0247; A61B 5/0004; A61B 5/0053; A61B 5/4255; A61B 5/4343; A61B 5/435; A61B 5/4356; A61B 5/4836; A61F 5/026; A61F 5/028; A61F 2013/00468; A61F 5/34; A61H 2201/163; A61H 1/024; A61H 1/0244; A61H 1/0266; A61H 2201/1215; A61H 2201/1616; A61H 2201/1623; A61H 2201/1642; A61H 2201/16; A61H 2201/165; A61H 3/00; A61H 3/008; A61H 1/0218; A61H 2201/162; A63B 21/0442; A63B 21/0552; A63B 21/1419; A63B 21/1449; A63B 2208/0204; A63B 21/143; A63B 21/00185; A63B 21/0557; A63B 21/1434; A63B 21/00061; A63B 21/1438; A63B 21/1442; A63B 21/00
USPC ................................................ 602/19, 32–39
See application file for complete search history.

(56) References Cited

U.S. PATENT DOCUMENTS 1,336,910 A 4/1920 Bernarr
1,618,273 A * 2/1927 Davidson ........... A63B 21/0004 482/124

(Continued)

OTHER PUBLICATIONS

Engineers Edge, Yield Strength—Strength (Mechanics) of Materials, available at http://www.engineersedge.com/material_science/yield_strength.htm (retrieved Oct. 30, 2013), citing Machinery's Handbook, 29th Edition, published Jan. 2, 2012.

(Continued)

*Primary Examiner* — Michael Brown

(57) ABSTRACT

The invention provides a spinal therapy device that can be used by an individual to self-apply overpressure, spinal decompression, spinal joint mobilization or a combination thereof to the spine, as well as methods for using a spinal therapy device to self apply overpressure, spinal decompression, spinal joint mobilization or a combination thereof.

20 Claims, 22 Drawing Sheets

(51) Int. Cl.

| | |
|---|---|
| ***A63B 21/002*** | (2006.01) |
| ***A63B 21/04*** | (2006.01) |
| ***A63B 21/055*** | (2006.01) |
| ***A63B 21/068*** | (2006.01) |
| ***A63B 23/02*** | (2006.01) |
| ***A63B 23/035*** | (2006.01) |
| ***A61H 1/02*** | (2006.01) |
| ***A63B 21/16*** | (2006.01) |
| *A63B 7/00* | (2006.01) |

(52) U.S. Cl.
CPC ........ *A63B 21/4009* (2015.10); *A63B 21/4025* (2015.10); *A63B 21/4034* (2015.10); *A63B 21/4035* (2015.10); *A63B 21/4043* (2015.10); *A63B 23/0211* (2013.01); *A63B 23/0222* (2013.01); *A63B 23/03541* (2013.01); *A63B 23/03575* (2013.01); *A61H 2201/1253* (2013.01); *A61H 2201/163* (2013.01); *A61H 2201/164* (2013.01); *A61H 2201/1652* (2013.01); *A63B 7/00* (2013.01); *A63B 2208/0204* (2013.01); *A63B 2208/0252* (2013.01); *A63B 2208/0261* (2013.01)

(56) References Cited

U.S. PATENT DOCUMENTS

| | | | | |
|---|---|---|---|---|
| 2,280,274 | A | | 4/1942 | Wildermuth |
| 4,735,412 | A | | 4/1988 | Prsala |
| 4,909,505 | A | | 3/1990 | Tee |
| 5,086,759 | A | | 2/1992 | Buddingh |
| 5,143,057 | A | | 9/1992 | Depasquale |
| 5,167,602 | A | | 12/1992 | Lehktman |
| 5,207,627 | A | | 5/1993 | Doran |
| 5,242,377 | A | | 9/1993 | Boughner et al. |
| 5,248,293 | A | | 9/1993 | Hubbard et al. |
| 5,258,017 | A | | 11/1993 | Myers et al. |
| 5,314,404 | A | | 5/1994 | Boughner et al. |
| 5,362,295 | A | * | 11/1994 | Nurge .............. A63B 21/00061 482/121 |
| 5,372,565 | A | * | 12/1994 | Burdenko ............... B63C 9/135 482/124 |
| 5,509,869 | A | | 4/1996 | Miller |
| 5,518,486 | A | | 5/1996 | Sheeler |
| 5,588,941 | A | | 12/1996 | Scott |
| 5,813,955 | A | | 9/1998 | Gutkowski et al. |
| 6,875,135 | B2 | | 4/2005 | Tracy, Sr. |
| 6,923,750 | B1 | | 8/2005 | Hinds |
| 7,037,284 | B2 | | 5/2006 | Lee |
| 7,044,896 | B2 | | 5/2006 | Hetrick |
| 7,083,557 | B2 | | 8/2006 | Phipps |
| 7,628,742 | B2 | * | 12/2009 | Weaver .............. A63B 21/0004 482/124 |
| 7,757,305 | B2 | | 7/2010 | Toso |
| 7,878,996 | B2 | | 2/2011 | Smith, Jr. |
| 2003/0130098 | A1 | * | 7/2003 | Marco ................ A63B 21/0004 482/124 |
| 2007/0099774 | A1 | | 5/2007 | Bruback |
| 2007/0232973 | A1 | | 10/2007 | Serola |
| 2008/0188788 | A1 | | 8/2008 | Serola |
| 2008/0200853 | A1 | | 8/2008 | Tielve |
| 2012/0123310 | A1 | | 5/2012 | Gazayerli |

OTHER PUBLICATIONS

Godino, J., Climbing Gear Strength Ratings, Mazamas, Feb. 2006, available at http://mazamas.org/resources/climbing-gear-strength-ratings/ (retrieved Dec. 10, 2013).

* cited by examiner

SPINAL THERAPY DEVICE

CROSS-REFERENCE TO RELATED APPLICATIONS

This application claims priority to U.S. provisional patent application Ser. No. 61/752,699, filed Jan. 15, 2013, the contents of which is incorporated herein by reference in its entirety.

BACKGROUND

Low back pain is a common disorder affecting the quality of life and productivity of a large proportion of the population in the industrialized countries and contributing significantly to health care expenditures. A significant number of individuals with acute back pain develop chronic low back pain resulting in reduced physical function, social participation, psychological distress and poorer quality of life. Recurrences of lower back pain and associated functional limitations often can be managed with physical therapy and exercise. Manual therapies such as manual traction, overpressure and spinal joint mobilization, for example, which create posterior-to-anterior pressure directed to a specific region on the spine, are commonly used to treat low back pain. Currently, these techniques are performed by skilled clinicians during treatment sessions that occur two to three times a week. Given their effectiveness for alleviating back pain, it is desirable to enable the individual back pain sufferer to self-administer these techniques as needed.

SUMMARY OF THE INVENTION

The invention provides a portable device that can be used by an individual to self-administer therapeutic exercises or treatment to a selected region on the spine. The device of the invention allows the user to self-administer spinal decompression, overpressure or joint mobilization to a select spinal segment of the lower back in a controlled manner and as frequently as desired.

In one aspect, the invention provides a spinal therapy device having: (a) a belt for fastening around a user's lumbar region, the belt having a belt fastening assembly for detachably securing the effective ends of the belt together; (b) a length-adjustable anchor strap, one end of which is coupled to the belt, the other end comprising an anchor effective to receive a user's foot, the strap being coupled to the front of the belt when the belt is fastened on the user; and (c) a first and a second resistance member, each coupled to the belt at one end and comprising a handle at the other end.

In some embodiments, the anchor strap, resistance members, or both anchor strap and resistance members are detachably coupled to the belt. In some embodiments, the resistance members are slidably coupled to the belt. In some embodiments, the belt is composed of leather, nylon, canvas, rubber, plastic, cotton, polyvinyl chloride, polyester or polypropylene or a combination thereof.

In some embodiments, the belt fastening assembly includes a hook and loop fastener, one member of which is attached to an end portion of the belt on the belt's exterior face, and the complementary member of which is attached to the other end portion of the belt on the belt's interior face such that when the belt is wrapped around the user's lumber region, the complementary hook and loop fastener members on opposing surfaces of the overlapping portions adhere thereby fastening the belt around the user. In some embodiments, the belt fastening assembly includes a ring having any regular or irregular shape. In some embodiments, the belt fastening assembly includes an oval, circular, D-shape, square or rectangular ring. In some embodiments, each end of the belt is inserted through the ring opening and folded back to form a loop maintained by securing a portion of the inserted section of the belt to a portion of the uninserted section of the belt, the ring thereby forming a link between the effective ends of the belt. In some embodiments, the ring comprises two openings, wherein the ends of the belt are inserted through the first opening, while one end of the anchor strap is inserted through the second opening, and wherein each inserted section is folded back to form a loop maintained by securing a portion of the inserted section to a portion of the corresponding uninserted section, the ring thereby joining the effective ends of the belt together around the user, while coupling the anchor strap to the lumbar belt. In some embodiments, the ring comprises three openings, wherein one end of the belt is inserted through the first opening, the other end of the belt is inserted through the second opening, and one end of the anchor strap is inserted through the third opening, and wherein each inserted section is folded back to form a loop maintained by securing a portion of the inserted section to a portion of the corresponding uninserted section, the ring thereby joining the ends of the belt together around the user and coupling the anchor strap to the lumbar belt. In some embodiments, the belt fastening assembly includes two rings that are oval, circular, D-shape, square or rectangular. In some embodiments, the belt fastening assembly includes a prong buckle secured to a first end of the belt and one or more holes for receiving the prong on a second end portion of the belt. In some embodiments, the belt fastening assembly includes a quick-release buckle and an adjustable slide or fixed threading plate, and wherein each end of the belt is inserted though a slot on a member of the quick-release buckle, then secured to a portion of the corresponding uninserted section.

In some embodiments, the anchor strap is coupled to the belt through a loop formed at one end of the anchor strap, wherein the loop is maintained by securing a portion of the strap on one side of the belt to a portion of the strap on the other side of the belt, and wherein the loop transversely encircles the belt enabling the anchor strap to hang from the belt. In some embodiments, the portions are secured by stitching, a hook and loop fastener, an adjustable slide, a fixed threading plate, or one or more snaps.

In some embodiments, the anchor strap, resistance members or anchor strap and resistance members are coupled to the belt through one or more connectors. In some embodiments, the one or more connectors comprise a ring, flexible loop, clip, snap, hook, buckle or any combination thereof.

In some embodiments, the ring is circular, oval, square or rectangular. In some embodiments, the ring is a split ring. In some embodiments, the ring has an opening through which the belt and resistance members are inserted. In some embodiments, the ring has an opening through which each end of the belt and one end of the anchor strap are inserted, and wherein each inserted end is folded back to form a loop maintained by securing a portion of the inserted section to a portion of the corresponding uninserted section, the ring thereby joining the effective ends of the belt together around the user and coupling the anchor strap to the belt. In some embodiments, the ring has two openings, wherein the belt is inserted through one opening, and the anchor strap is inserted through the other opening, thereby coupling the anchor strap to the belt. In some embodiments, the ring has two openings, wherein both ends of the belt are inserted through the first opening and then folded back, each on itself, to form a loop maintained by securing a portion of the inserted section to a portion of the corresponding uninserted section, the ring thereby joining the effective ends of the belt together around the user; and wherein one end of the anchor strap is inserted through the other opening and then folded back to form a loop maintained by securing a portion of the inserted section to a portion of the corresponding uninserted section, thereby coupling the anchor strap to the belt.

In some embodiments, the flexible loop is sewn on the belt. In some embodiments, the flexible loop is made of the same material as the belt.

In some embodiments, the anchor strap is coupled to the belt through a ring, flexible loop or a buckle to which a clip or snap is linked; wherein the ring, flexible loop or buckle comprises an opening through which the belt is inserted; and wherein the clip or snap comprises a fixed or swivel bail or shackle to which the anchor strap is secured. In some embodiments, the anchor strap is secured to the fixed or swivel bail or shackle through a loop formed by inserting one end of the anchor strap through the bail or shackle and then securing a portion of the inserted section of the strap to a portion of the uninserted section of the strap, thereby enabling the strap to hang from the fixed or swivel bail or shackle.

In some embodiments, the portions of the belt or strap are secured by stitching, a hook and loop fastener, an adjustable slide, a fixed threading plate, one or more snaps, or any combination thereof.

In some embodiments of a spinal therapy device of the invention, each resistance member is coupled to the belt through a ring, flexible loop or a buckle to which a clip or snap is linked; wherein the ring, flexible loop or buckle includes an opening through which the belt is inserted; and wherein the clip or snap includes a fixed or swivel eye, bail or shackle to which the resistance member is secured. In some embodiments, the one end of the resistance member is inserted through the eye, bail or shackle. In some embodiments, the resistance member is secured to the clip or snap through a connector with a reinforced eyelet through which one end of the resistance band or tubing can be inserted. In some embodiments, the ring is a split ring. In some embodiments, the clip is a trigger hook, wire lever clip, carabiner clip, Bimini clip, harness clip or spring clip. In some embodiments, the one or more connectors is composed of metal, leather, canvas, rubber, plastic, polyvinyl chloride, polypropylene, polyester or a combination thereof. In some embodiments, the one or more connectors is composed of an alloy or stainless steel.

In some embodiments of a spinal therapy device of the invention, the anchor strap is coupled to the belt through a ring or buckle in the belt fastening assembly. In some embodiments, the anchor strap includes two strap segments detachably connected end to end, and wherein at least one segment is length-adjustable. In some embodiments, the two strap segments are connected by a quick-release or cam buckle. In some embodiments, one end of the length-adjustable segment is connected to the buckle by insertion through a slot on the buckle and then folding back to form a loop maintained by a hook and loop fastener, an adjustable slide, a fixed threading plate, one or more snaps, or any combination thereof that secures a portion of the inserted section to a portion of the uninserted section of the length-adjustable segment.

In some embodiments, the anchor is a loop effective to engage a user's foot. In some embodiments, the loop is formed by securing the end of the anchor strap to another portion of the anchor strap so as to form a loop having an opening effective to engage a user's foot. In some embodiments, the end of the anchor strap is secured to another portion of the anchor strap by stitching. In some embodiments, a section of the loop is encased in a rigid material to facilitate grip. In some embodiments, the material is polyurethane, plastic, rubber, ethylene vinyl acetate or a combination thereof.

In some embodiments, the anchor is a rigid elongated member secured to the anchor strap. In some embodiments, the rigid elongated member is secured to the anchor strap though a loop formed by the anchor strap, the loop having a central opening through which the rigid elongated member is inserted thereby forming two arms extending outwardly in opposing direction and away from the anchor strap. In some embodiments, the two arms extend outwardly and upwardly away from the anchor strap. In some embodiments, the two arms extend perpendicularly away from the anchor strap.

In some embodiments of a spinal therapy device of the invention, the handle of the resistance member is formed by securing the end portion of the resistance member to another portion to form a loop. In some embodiments, the portions are secured using a spring-loaded locking mechanism. In some embodiments, a section of the loop is encased in a rigid material to facilitate grip. In some embodiments, the material comprises polyurethane, plastic, rubber, ethylene vinyl acetate or a combination thereof. In some embodiments, the handle is removably attached to the resistance band. In some embodiments, each resistance member includes a loop at one end that transversely encircles the belt thereby coupling the resistance member to the belt, wherein the loop is formed by securing an end portion of the resistance member to another portion.

In some embodiments of a spinal therapy device of the invention, the lumbar belt includes an elastic member detachably secured to the posterior section of the belt on its exterior face when the belt is fastened on the user. In some embodiments, the elastic member is detachably secured to the belt through a hook and loop fastener. In some embodiments, the elastic member extends substantially across the posterior section of the belt.

In some embodiments of a spinal therapy device of the invention, a detachable pouch is coupled to the lumbar belt, the detachable pouch having a pocket for receiving a therapeutic device and a fastener for securing the pouch to the interior face of the belt. In some embodiments, the fastener is a hook and loop fastener. In some embodiments, the therapeutic device is a cold pack, a hot pack, a vibration device or an acupressure ball.

In another aspect, the invention provides a spinal therapy device having a belt for fastening around a user's lumbar region, the belt having: (a) a belt fastening assembly for fastening the belt around a user's lumber region; (b) optionally, a separate anchor strap connector for coupling an anchor strap to the belt, wherein the anchor strap connector and a coupled anchor strap are effective to support a load of at least 50 pounds; and (c) a first and a second resistance member connector for removably coupling a first and a second resistance band, respectively, to the belt, wherein the first and second resistance band connectors enable independent placement of the attached resistance bands at select positions around the belt, and wherein the first and second resistance band connectors are effective to support a load of 50 pounds. In some embodiments, the anchor strap connector, resistance band connector or both anchor strap connector and resistance band connector is a split ring, closed ring, flexible loop, clip or snap. In some embodiments, the device also includes two resistance bands, each of which is detachably coupled to the belt through the resistance band connector. In some embodiments, the device further includes an anchor strap detachably coupled to the belt through the anchor strap connector.

In another aspect, the invention provides a method for applying overpressure to a lower back region of an individual that involves fastening a device of the invention to the lumbar region of the individual and applying overpressure through the belt by extending the resistance bands coupled to the belt so as to produce a posterior-to-anterior force directed into the back of the individual. In some embodiments, overpressure is applied by extending the resistance members upwardly toward the head of the individual and maintaining a downward force through engagement of the individual's foot with the coupled anchor strap, wherein the effective length of the anchor strap corresponds to the distance between the belt and the individual's foot. In some embodiments, the method further includes applying decompression to the spine by flexing the foot engaged with the anchor member. In some embodiments, the resistance members are extended outwardly away from the front of the body of the individual so as to generate a force that is perpendicular to the spine. In some embodiments, the method is performed while the individual is in a standing position, a prone position, a prone on elbows position, a prone press-up position or a supine knee-to-chest position.

In another aspect, the invention provides a method for applying overpressure to a lower back region of an individual that involves fastening a device of the invention to the lumbar region of an individual and applying overpressure through the belt by exerting a posterior-to-anterior force directed into the back of the individual through the coupled anchor strap. In some embodiments, the force is generated by the individual leaning backwards over the lumbar belt as the individual is supported by the anchor strap coupled to the lumbar belt at one end and secured at the other end between a closed door and the doorframe. In some embodiments, the force is generated by the individual extending backwards over the lumbar belt as the belt is maintained in position by the individual's foot engaging with the anchor member of the anchor strap, wherein the effective length of the anchor strap corresponds to the distance between the belt and the user's foot. In some embodiments, the method further includes applying decompression to the spine by flexing the foot engaged with the anchor member. In some embodiments, the method further includes applying spinal joint mobilization by attaching a vibration device between the lumbar belt and the lower back of the individual.

In another aspect, the invention provides a method for alleviating lower back discomfort that involves fastening a belt to the lumbar region of an individual at a position that corresponds to the area of discomfort, maintaining the position of the belt on the lumbar region, and applying a force into the lower back of the individual through the belt, wherein the force is effective to generate overpressure, decompression, joint mobilization or a combination thereof at a select spinal segment. In some embodiments, the position of the belt is maintained by the individual's foot engaging with the anchor member of an anchor strap coupled to the lumbar belt, the anchor strap having an effective length extending from the belt to the individual's foot. In some embodiments, the force is applied by extending the resistance member coupled to the belt. In some embodiments, the force is applied by flexing the foot engaged with the anchor strap. In some embodiments, the force effective to achieve joint mobilization is generated using a vibrating device attached between the belt and the lower back.

The spinal therapy device of the invention is particularly effective for applying overpressure or spinal decompression to a selected spinal segment as it shifts minimally during use allowing the user to maintain directional force perpendicular or parallel to the spine, thereby minimizing shearing between vertebra. The correct directional force can provide overpressure to the joint, relieve pain and promote greater range of motion. In addition, the coupled anchor strap allows the user to provide downward traction to the spine and control the amount of traction by plantar flexing the user's foot. As the device allows the user to target or isolate a select spinal segment, the user is more likely to achieve end range of motion. Furthermore, the anchor strap coupled to the belt can be used to support the user during spinal therapy exercises thereby allowing the user to relax the lumbar spine musculature, which results in less muscle guarding, less muscle spasm and greater range of motion. The slidably coupled resistance members in combination with the coupled anchor strap allow for increased versatility of the device, in particular, core strengthening exercises can be applied, unilateral directional forces can be applied more easily, and illiotibial band stretch can be performed in a standing or supine position. The present invention also enables the coupling of spinal joint mobilization (decreases pain and promotes increase range of motion) with spinal therapy exercises by providing an attached joint mobilizer, as well as use of a hot or cold pack during spinal therapy exercises. The present invention, being easily and detachably secured to a closed door, has the advantage of being portable and versatile. In addition, prior art devices can be difficult to don and doff, requiring the user to bend and twist uncomfortably compromising the integrity of the spine. The device of the invention allows for convenient donning and doffing with no bending and twisting maintaining spinal integrity before and after use of the product.

Any feature or combination of features described herein are included within the scope of the present invention provided that the features included in any such combination are not mutually inconsistent as will be apparent from the context, this specification and the knowledge of one of ordinary skill in the art.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used to practice the invention, suitable methods and materials are described below.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Other features and advantages of the invention will be apparent from the following detailed description and from the claims.

DETAILED DESCRIPTION OF THE INVENTION

Figure 1:
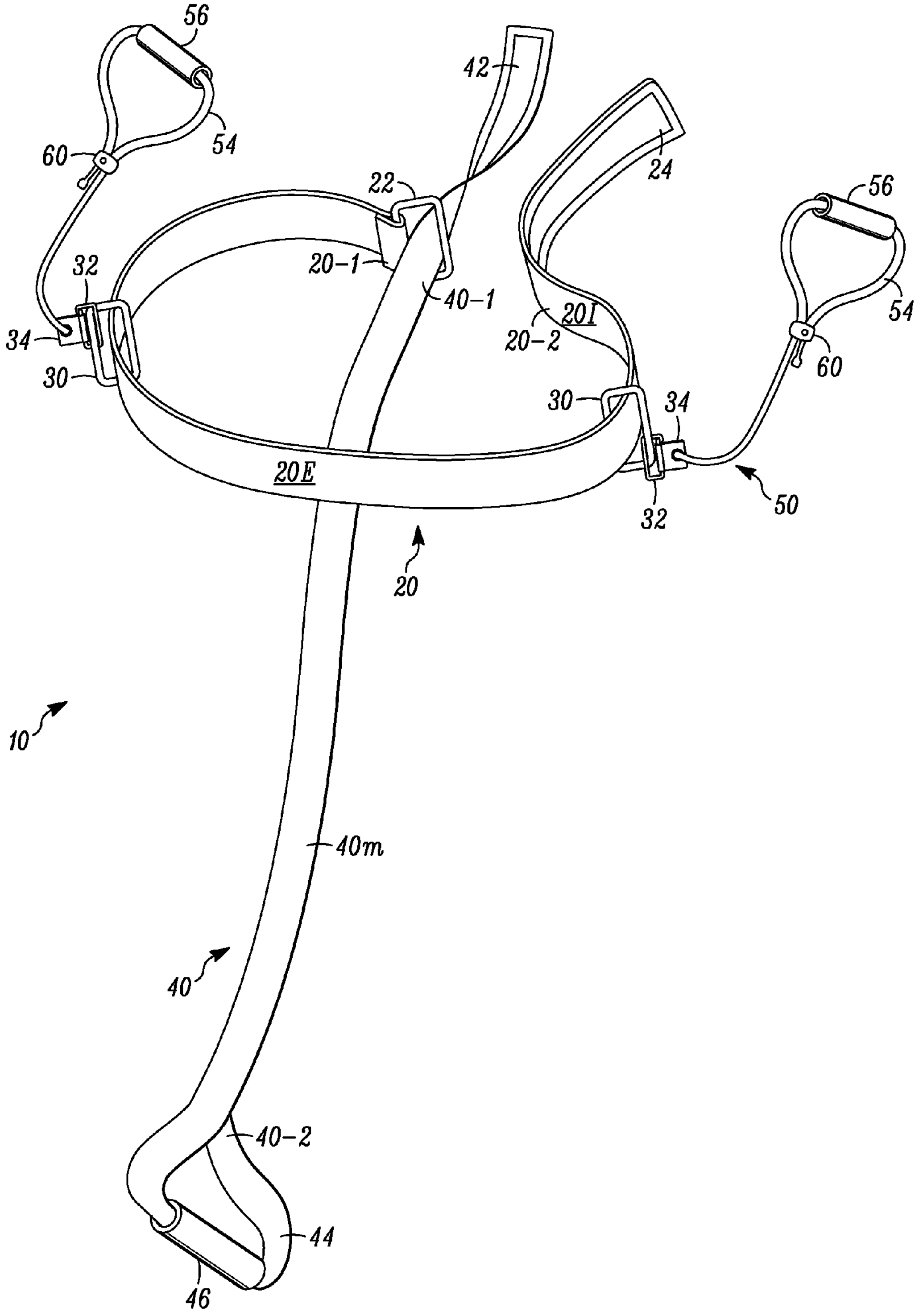
FIG. 1 is a rear perspective view of a spinal therapy device of the invention that includes belt 20, anchor strap 40 and two resistance members 50.

The invention provides a portable, spinal therapy device that allows the user to perform a variety of exercises beneficial to the lower back. A device of the invention includes a belt having one or more connectors that allow the belt to be used with an anchor strap and two resistance members. The belt can be fastened around the lumber region (region of the torso between the diaphragm and the sacrum) of various users. The anchor strap can be coupled to the belt using one or more connectors that allow the anchor strap to be securely attached to, or conveniently detached from, the belt as desired by the user. Two resistance members can be coupled to the belt using one or more connectors that allow each resistance members to be coupled to the belt at a convenient position along the circumference of the belt when worn by the user. The device of the invention can be used to perform a variety of exercises that involve the application of spinal decompression, overpressure, spinal joint mobilization or a combination thereof at the same time to a select region of the lower back or select spinal segment.

Belt

Any commonly used belt that can be fastened around an individual's waist or for securing garment to an individual's waist can be used in a device of the invention. In general, a belt for use in a device of the invention has an elongated structure with a first end and a second end that can be fastened together using a belt fastening assembly. The belt can have any convenient width that allows the belt to isolate or engage with a spinal segment to be treated. A spinal segment includes two vertebrae, the intervertebral disc separating the two vertebrae, the nerves that leave the spinal cord at that level and the facet joints that link each level of the spinal column. Thus, the belt can be about one to three inches wide, for example, about 1¼ to about 2¼ inches wide, about 2¼ to about 3¼ inches wide, about 3¼ to about 4¼ inches wide. A belt of the invention can be, for example, about 1¼, about 1½, about 1¾, about 2, about 2¼, about 2½, about 2¾, or about 3 inches wide. The belt can also have any convenient length so long as it can be fastened around the lumber region of a user or users of various sizes. The belt can be about 24 inches to about 50 inches long, for example, about 26, about 28, about 30, about 32, about 34, about 36, about 38, about 40, about 42, about 44, about 46, about 48 or about 50 inches long. The belt can be made of a flexible, elastic or inelastic material, including, without limitation, natural or synthetic leather, suede, canvas, cotton, flax, plastic, natural or synthetic rubber, nylon, polyvinyl chloride, polyester, polypropylene, other natural or synthetic fabric or webbing, or any combination thereof.

The belt includes a belt fastening assembly for securing the effective ends of the belt together around a user. As used herein, the term "effect ends," in reference to a belt, refers to the two regions, one on each end portion of the belt, that come together to define the circumference of the belt when the belt is fastened around a user. Any devices known to those of skill in the art that can be used to secure two effective ends of the belt together can be used. A belt fastening assembly can include, without limitation: a prong buckle, i.e. a buckle with frame, bar and prong for insertion into one or more holes on other end portion of the belt; a quick-release buckle such as a side- or end-release buckle; an over-center, ratchet or cam buckle; a hook and loop fastener (i.e., a strip of hooks and a strip of loops that adhere when pressed together); a ring of any shape including round, oval, D-shape, and square or rectangular ring with one, two, three or more openings; an adjustable slide or fixed threading plate; one or more buttons that cooperate with one or more holes, loops or retaining pins on other end portion of the belt; one or more hook-and-eye closures; one or more snap fasteners (such as press studs); or any combination thereof.

In many embodiments, the belt fastening assembly allows the belt to be adjusted to fit different users. Where a quick-release buckle is used to secure the effective ends of the belt around the user, the male buckle member can be secured to one end of the belt, and the female buckle member can be secured to the other end of the belt. To allow the user to adjust the circumference of the belt, one member of the buckle (male or female) can be fixed to a first end of the belt, while the other member can be slidably secured to the other end portion of the belt, thereby enabling the circumference of the belt to be adjusted by adjusting the position of the other member. Similarly, when a prong buckle is used, the prong buckle can be fixed to one end of the belt, while the other end portion of the belt can include one or more holes into which the buckle prong can be inserted. In these embodiments, the user adjusts the circumference of the belt by selecting the hole into which the buckle prong is inserted. Where a hook and loop fastener is used, the hook and loop fastener can be used alone or in cooperation with a ring having one or more openings (FIGS. 1 & 2). For example, one member of a hook and loop fastener can be attached to the exterior surface of the first end portion of the belt, while the complementary member can be attached to the interior surface of the other end portion. When the belt encircles the user's lumbar region, where the end portions of the belt overlap, the complementary members of the hook and loop fasteners are on opposing surfaces and when pressed together, the complementary members adhere one to the other thereby fastening the belt to the user's lumbar region. The circumference of the belt can be decreased or increased by increasing or decreasing the region of overlap, respectively. A hook and loop fastener can also be used in cooperation with a ring (FIGS. 1 & 2). A ring of any shape (e.g. D shape, O shape, square shape, rectangular shape) having one, two or three openings, for example, can be fixed to the first end of the belt, while complementary members of hook and loop fasteners can be attached in series to the exterior surface of the second end portion of the belt. In this case, when the second end portion of the belt is passed through the ring and then folded back on itself, the complementary hook and loop fasteners are pressed together and adhere, thereby securing the two ends of the belt together. In another embodiment, one or more buttons can be affixed on a first end of belt, while one or more holes, loops or pins can be affixed on the other end of belt. In these embodiments, the belt can be configured to accommodate users of various sizes by inclusion of one or two buttons at one end of the belt and multiple holes, loops or pins spaced at convenient intervals at the other end of the belt for engaging with the one or more buttons. Alternatively, multiple buttons spaced at intervals away from one end of the belt can be used with one or two holes, loops or pins at the other end of the belt. Hook and eye closures or snap fasteners can be arranged as described for buttons-holes, loops or pins combination to allow the belt to accommodate users of different sizes.

The belt can have an anchor strap connector and two resistance member connectors. The connectors allow for convenient attachment of an anchor strap or resistance band or tubing to the belt and, in some embodiments, easy detachment from the belt as desired by the user. Any device that allows an elongated strap, band or tubing to be attached to the belt can be used. Any device that allows an elongated strap, band or tubing to be easily, but securely attached to, or detached from, the belt can be used as an anchor strap or resistance member connector including the belt fastening mechanisms described above for securing the two ends of the belt together.

The anchor strap connector can have a rigid structure with a regular or irregular, or symmetric or asymmetric shape or opening. The anchor strap connector can be a circular, oval, triangular, square, rectangular or D-shape ring or link. The connector can also have a flexible loop structure such as a fabric, leather, rubber, plastic or webbed loop sewn on or encircling the belt. The anchor strap connector can be substantially inelastic, but flexible and bendable so that when a load is applied through the anchor strap, the load is transferred to the belt via the anchor strap connector. The anchor strap connector can hang from the belt at any position or it can be fixed at one position on the belt. In some embodiments, the belt fastener can function as an anchor strap connector. Where the belt fastener includes a ring or buckle, for example, the ring or buckle frame can be used to couple the anchor strap to the belt. In these embodiments, the connector can have an opening wide enough for one or both ends of the belt and, optionally, the anchor strap, to pass through. The connector can have two openings, one for the ends of the belt to be inserted through, and the second opening for the anchor strap to be inserted through (FIG. 2C). The connector can also have three openings, one opening for each end of the belt and a third opening for the anchor strap (FIG. 2B). In other embodiments, the anchor strap connector can be separate and independent of the belt fastener. For example, the anchor strap connector can be a loop or ring that hangs from, is sewn on or otherwise secured to the belt and to which one end of the anchor strap can be attached using any method or device known to those of skilled in the art as discussed further below. The connector can hang from the belt, and in some embodiments, can form a link between the belt and the anchor strap or resistance member. The anchor strap connector can be a female member of a quick-release clip secured to the belt and to which the male member on one end of the anchor strap can be clipped; or a male member of a quick-release clip secured to the belt and to which the female member on one end of the anchor strap can be clipped. The anchor strap connector can be made of any material of sufficient strength to maintain the integrity of the spinal therapy device during use. For example, when the anchor strap, coupled to the belt worn on a user, is secured to a fixed structure, the resulting device is effective to sustain at least the weight of the user wearing the belt. Thus, the anchor strap connector can be made natural or synthetic leather, suede, canvas, cotton, flex, natural or synthetic rubber, plastic, nylon, polyvinyl chloride, polyester, polypropylene, other natural or synthetic fabric, polymer, plastic or webbing, one or more metal or an alloy such as steel, or a combination thereof, so long as the connector is sufficiently inelastic such that when a load is applied through the anchor strap, the load can be transferred to the belt via the anchor strap connector. The anchor strap connector can be made of the same material as, or different material from, the belt or anchor strap. Connectors are substantially inelastic, but flexible and bendable so that when a load is applied through the resistance members or anchor strap, the load is transferred to the belt via the connecting members.

The resistance member connector can have a rigid structure with a regular or irregular, or symmetric or asymmetric shape or opening. The resistance member connector can be a circular, oval, triangular, square, rectangular or D-shape ring or link. The connector can also have a flexible loop structure such as a fabric, leather, rubber, plastic or webbed loop sewn on or encircling the belt. The resistance member connector can be substantially inelastic, but flexible and bendable so that when a load is applied through the resistance members, the load can be transferred to the belt via the resistance member connector. The resistance member connector can be slidably attached to the belt, i.e. it is slidable along the length of the belt and can be positioned at any point between the first end of the belt and the second end of the belt allowing the attached resistance member to be positioned at any convenient point around the belt during use. The resistance member connector can be slidably attached each to an effective end portion of the belt so that it can be positioned on the left or right anterior portion of the belt when the belt is worn on the user. The resistance member connector can be attached to the belt one on each side section of the belt worn on the user such that the resistance members coupled to the connectors hang substantially at the sides of the user's body, i.e. substantially next to the user's arms or between the user's arms and the sides of the user's body. The resistance member connector can have an opening through which the belt, and optionally, the resistance member, can pass freely allowing the connector to hang from the belt, and in some embodiments, forming a link between the belt and resistance member. Thus, the resistance member connector can be configured to allow a resistance member to directly attach to it, for example, by hanging from the connector, or indirectly attached to it, for example, through a ring, hook, snap, clip, carabiner or any connectors described herein. The resistance member connector can be made of any convenient material having sufficient strength to sustain the resistance force exerted by the user on the resistance member. The resistance member connector can be made of natural or synthetic leather, suede, canvas, cotton, flex, natural or synthetic rubber, plastic, nylon, polyvinyl chloride, polyester, polypropylene, other natural or synthetic fabric, polymer, plastic or webbing, one or more metal or an alloy such as steel, or a combination thereof, so long as the connector is sufficiently inelastic such that when a load is applied through the resistance members, the load can be transferred to the belt via the resistance member connector. The connector can be made of the same material as, or different material from, the belt or resistance member.

Anchor Strap

A spinal therapy device of the invention can include an anchor strap for use with the belt to limit movement of the belt on the wearer during use. The anchor strap allows the user to control the counter force of the resistance members with the user's foot to create an optimal directional force for achieving overpressure or decompression. For example, it allows the user to maintain a directional force about perpendicular to the spine (i.e. about congruent with the joint line of each vertebra) as needed for generation of overpressure. It also allows the user to generate a downward or linear directional force about parallel to the spine using the user's foot as needed for spinal decompression and distraction of the joint. The anchor strap can also be used to anchor or secure the spinal therapy device to a fixed structure such as a door as needed. The anchor strap is coupled to the belt at one end and forms or is attached to an anchor member on the other end.

The anchor strap can be made of any flexible and elastic or inelastic material. The anchor strap and can have any convenient width and thickness so long as the anchor strap can support the weight of the user. The anchor strap can be made of the same, similar or a different material than that of the belt. Thus, the anchor strap can be made of any flexible material, including, without limitation, natural or synthetic leather, suede, canvas, cotton, flax, plastic, natural or synthetic rubber, nylon, polyvinyl chloride, polyester, polypropylene, other natural or synthetic fabric or webbing, or any combination thereof. The anchor strap can be any convenient length so long as when fastened to the belt, the anchor strap has effective length between about 36 inches to about 60 inches. Thus, the effective length of the anchor strap can be about 36 inches, about 39 inches, about 48 inches, about 51 inches, about 54 inches, about 57 inches or about 60 inches. The anchor strap can have any convenient width or thickness so long as the strap is effective to support the weight of the user. Thus, the anchor can have a width of, for example, at least about 1 inch, for example, about 1.25 inches, 1.5 inches, 1.75 inches, 2 inches, 2.25 inches, 2.5 inches, 2.75 inches, 3 inches, 3.25 inches, 3.5 inches, 3.75 inches, 4 inches or more than 4 inches wide.

The anchor strap can be directly or indirectly coupled to the belt. One end portion of the anchor strap can form a loop that encircles the belt transversely allowing the anchor strap to hang directly from the belt. That is, one end portion of the anchor strap can be inserted behind a section of the belt then folded over the belt thereby forming a loop transversely encircling a section of the belt. The loop can be maintained by securing a portion of the strap on one side of the belt (e.g. behind the belt) to a portion of the strap on the other side of the belt (e.g. in the front of the belt) as described further below. Such a loop can allow the anchor strap to hang directly from the belt. Alternatively, the anchor strap can be indirectly coupled to the belt at one end through one or more connectors that, optionally, allow the strap to be conveniently detached from the belt as needed. For example, the belt and strap can be linked using a ring, clip or a combination of a ring and clip. Connectors are further discussed below.

The other end of the anchor strap includes an anchor member through which the user can limit movement of the belt on the user during use or apply spinal decompression during use. For example, when a user extends the resistance members coupled to the belt in an upward direction, the belt to which the resistance members are coupled is tugged upward. The user can limit the upward shifting of the belt by maintaining a force in the downward direction using the anchor strap coupled to the belt. The anchor strap, coupled to the belt and adjusted so it extends only to the user's foot, is held in place by the user's foot engaging with the anchor member thereby limiting the belt's movement upward as the resistance members coupled to the belt are extended in an upward direction by the user. Engagement of the user's foot with the anchor strap also generates a downward force causing immediate decompression of the spine as further described below. In another embodiment, the anchor member of the strap can be used to anchor the strap and belt to a closed door. More specifically, the anchor strap can be placed on the top of a door so that the anchor member is on the other side of the door. When closed, the anchor strap is wedged between the door and door frame, while the anchor member remains on the other side of the closed door thereby anchoring the strap and belt to the door and frame structure. In yet another embodiment, the anchor member enables the foot that is engaged to the anchor member to generate a force by flexing that is transmitted through the anchor strap to the belt thereby applying decompression or traction to the spine. The anchor member can have any configuration or shape such as a flexible loop or rigid bar or hook sufficient to function as described above, for example, to allow a user to maintain a foothold. The anchor member can be a simple loop formed by turning the end of the strap toward itself and then securing a portion of the end of the strap to another portion of the strap of sufficient distance away so as to form a loop of sufficient size to accommodate a user's foot. The end of the loop can be secured to the main body using any means known to those of skill in the art as discussed above. A section of the anchor loop can be reinforced for increase strength, rigidity or resilience using any means known to those of skill in the art including encasing in a hard plastic material. In these embodiments, the anchor member can be made of the same material as the anchor strap. The anchor loop so formed may also be reinforced by encasing a section of the loop with a hard plastic material. Alternatively, the anchor member can have rigid structure made of a different material than the anchor strap. For example, the anchor member can be a substantially round or flat bar or crescent-shaped member made of any rigid material such as foam, wood, metal or plastic that can be secured to the end of the anchor strap using any means known to those of skill in the art. The rigid anchor member can be secured to the anchor strap by insertion through the opening of a loop formed by the end portion of the strap. The loop can be formed by stitching two portions of the strap so as to generate an opening through which the rigid bar or crescent-shaped member fits snuggly. Alternatively, the anchor strap can be inserted through an opening in the rigid anchor structure and then knotted on the inserted end or secured to a rigid stopper so as to retain the rigid anchor on the strap. In these embodiments, the anchor member at the end of the anchor strap provides a foothold that can engage with both feet to maintain the belt in a select position around the lumbar region of the user and provide spinal decompression during exercise progression.

The anchor strap can be a single strap having one end that is coupled to the belt and a second end that forms or is secured to the anchor member. Alternatively, the anchor strap can be composed of two or more anchor strap segments, at least one of which can be coupled to the belt and another terminating in the anchor member, attached end-to-end using any connectors know to those of skill in the art.

Any connectors or fasteners known to those of skill in the art can be used to couple the anchor strap to the belt or to secure one anchor strap segment to another. Examples of connectors that can be used for these purposes include, without limitation, a split ring (e.g. a ring of spring steel configured as two turns of a regular spring closely wound); closed ring that is round, oval, triangular, square, rectangular, D-shape or that have any convenient symmetrical or asymmetrical shape; a flexible loop; a quick link or connecting link; an adjustable slide or fixed threading plate; a wire lever clip, carabiner clip, as well as Bimini clip, harness clip or spring clip with or without slide lock, screw lock, auto lock or key lock; a spring gate snap, trigger snap, bolt snap, wire lever snap, snap shackle, without or without, fixed or swivel eye or bail; a utility hook, pelican hook with slide or slip hook with or without, fixed or swivel eye; or any combination thereof.

The connector for coupling the anchor strap to the belt can be a component of the belt fastening assembly such as the buckle or ring that joins the effective ends of the belt fastened around the user. For example, where a prong buckle is used as a connector, the strap can form a loop around the buckle frame allowing it to hang from the buckle frame. Where one or more rings are used to join the effective ends of the belt, the strap can be inserted through the opening(s) of the ring(s) thereby forming a loop allowing the strap to hang from the ring(s). The ring can have more than one opening, e.g. 2 or 3 openings, to separately accommodate the ends of the belt and the anchor strap or to separately accommodate each ends of the belt, as well as the anchor strap. The connector for coupling the anchor strap to the belt can also be a component distinct from the components in the belt fastening assembly and can be any device or mechanism through which the anchor strap can be attached to the belt. The connector for coupling the anchor strap to the belt, as well as the connector for joining two or more segments that form the anchor strap, can be a single unitary device such as a ring, loop or the like through which the strap can be attached to the belt, or a multi-member device such as a quick-release buckle, a hook and loop fastener, snaps or the like.

The connector for coupling the anchor strap to the belt can include an opening through which the belt is inserted. The connector for coupling the anchor strap to the belt can be otherwise secured to the belt, for example, by stitching as in the case of a belt loop or a rigid ring that has been sewn to the belt, thereby allowing an anchor strap attached to the connector to be coupled to the belt. Similarly, the connector for joining two segments of the anchor strap together can be secured to the end(s) of one or both segments by stitching. Where the belt or ends of the anchor strap or anchor segments are secured to a connector or a connector member by insertion through a slot or opening in the connector (or connector member) to form a loop, the loop can be maintained by securing a portion of the inserted section to a portion of the corresponding un-inserted section using any fastening means known to those of skill in the art including, without limitation, stitching, a hook a loop fastener, an adjustable slide, a fixed threading plate, one or more snaps or buttons, as well as any of the connectors discussed herein.

Where a two-member quick-release buckle is used to couple an anchor strap to the belt, one member of a quick-release buckle can be secured to the belt through a loop that is stitched to the belt, while the complementary member of the quick-release buckle can be secured to one end portion of the anchor strap. In this case, the loop on the belt is formed by insertion of the loop material through a slot on the first buckle member, then folded back and stitched to itself or the belt to permanently secure the buckle member to the belt. Similarly, the end of the anchor strap can be inserted through a slot in the complementary buckle member, then folded back to form a loop maintained by securing a portion of the inserted section of the strap to a portion of the corresponding un-inserted section of the strap. These portions can be secured using methods or devices known to those of skill in the art including, for example, by stitching or using a hook and loop fastener, adjustable slide, fixed threading plate, one or more snaps or the like. Where an adjustable slide or a fixed threading plate is used to couple the anchor strap to the belt, the slide or threading plate can be secured to the belt using a loop as described above for the quick-release buckle, while the end of the anchor strap can be inserted through the same slot or other slot on the slide or threading plate to form a loop that can also be maintained using any means known to those of skill in the art including, for example, by stitching or using a second slide, threading plate or one or more snaps. Where a ring is used to couple the anchor strap to the belt, both the anchor strap and belt can be inserted through one or more openings in the ring. In this case, a portion of the inserted section of the anchor strap can be secured to a portion of the uninserted section by stitching or using a hook and loop fastener, adjustable slide or fixed threading plate, one or more snaps or any means known to those of skill in the art. The ring can hang from the belt or can be secured to the belt using a loop stitched to the belt as described above. In these embodiments, the effective length of the anchor strap can be adjusted where the portions on the anchor strap are secured using a hook and loop fastener, adjustable slide, fixed threading plate, one or more snaps, or any other fastening means that enable the region of attachment to be adjusted.

Similarly, where a two-member quick-release buckle is used to join two or more anchor strap segments, one member of a quick-release buckle can be secured to the end of one segment, while the complementary member of the quick-release buckle can be secured to the end of the other segment. In this case, one end of a first segment can be inserted through a slot on the first buckle member, then folded back and stitched to a portion of the un-inserted section of the same segment to permanently secure the buckle member to the anchor strap segment. Similarly, one end of the second anchor strap segment can be inserted through a slot in the complementary buckle member, then folded back to form a loop maintained by securing a portion of the inserted section to a portion of the corresponding un-inserted section of the segment. These portions can be secured using methods or devices known to those of skill in the art including, for example, by stitching or using a hook and loop fastener, adjustable slide, fixed threading plate, one or more snaps or the like. Preferably, wherein one anchor strap segment is secured to a member of the quick-release buckle by stitching, the other segment is secured to the complementary member of the quick-release buckle using a hook and loop fastener, adjustable slide, fixed threading plate, one or more snaps or any other means known to those of skill in the art that allow the length of the strap segment to be adjusted. Where an adjustable slide or a fixed threading plate is used to join two anchor strap segments, the slide or threading plate can be secured to one segment by stitching as described above for the first member of the quick-release buckle, while one end of the other segment can be inserted through the same slot or other slot on the slide or threading plate to form a loop that can also be maintained as described above for the complementary member of the quick-release buckle. Where a ring is used to join two anchor strap segments, both anchor strap segments can be inserted through one or more openings in the ring. In this case, a portion of the inserted section can be secured to a portion of the uninserted section by stitching for one strap segment, for example. The portions on the inserted and un-inserted sections of the other segments can be secured using a hook and loop fastener, adjustable slide, fixed threading plate, one or more snaps or any means known to those of skill in the art that allow the other segment to be length adjustable. As such, the effective length of anchor strap can be adjusted to the user.

Where a hook and loop fastener is used to secure two portions of the anchor strap or anchor strap segments that come together to form a loop, the complementary members of the hook and loop fasteners are attached in series to the same face of the strap so that when the strap is folded back on itself, the complementary members are opposing and adhere. Where an adjustable slide or fixed threading plate is used to secure two portions of the anchor strap or strap segment that come together to form the loop, the strap is inserted through the first slot of the adjustable slide or fixed threading plate and threaded back through the second slot of the adjustable slide or fixed threading plate, before it is inserted through the anchor strap connector or a member of the anchor strap connector and re-inserted through the slots on the adjustable slide or fixed threading plate, thus securing a portion of the inserted section to a portion of the un-inserted section as shown in FIG. 3C. Where one or more snaps are used to the secure two portions of the anchor strap or anchor strap segments, one or more sockets and one or more studs can be secured to the same surface from the end of the anchor strap or strap segment arranged in a configuration analogous to the strips of hook and loop fasteners. A plastic safety guard can be used to cover the anchor straps attachment/adjustment site to promote safety and/or comfort.

Where the strap is directly coupled to the belt by forming a loop that encircles the belt transversely, a portion of the strap on one side of the belt can be secured to a portion of the strap on the other side of the belt as discussed above.

Where the effective length of the anchor strap or anchor strap segment is adjustable, the effective length can be shorten by increasing the length of the inserted section or lengthen by decreasing the length of the inserted section. The effective length of the anchor strap refers to the distance between where the strap is coupled to the belt to where the strap terminates with the anchor member.

The anchor strap can also be coupled to a common leather belt thereby providing convenience and versatility to the user.

Resistance Members

The spinal therapy device can include two resistance members, each of which is composed of an elongated resistance band or tubing of any useful size or tension that is coupled to the belt at one end and terminates in a handle on the other end. The resistance members can be coupled to the belt as discussed above with regards to resistance member connectors. Resistance members can be coupled to the belt on the anterior left and anterior right side of the belt so that by grasping the handles of the resistance members and stretching the resistance bands or tubings in an upward or downward direction away from the belt, or in any forwardly direction, the user applies a net force, through the belt, into a select region on the user's back. The term "forwardly," as used herein in reference to the direction in which the user's arms or resistance members are extended, means outward from the user's body toward the direction the user's torso is oriented and at any angle as shown in FIGS. 15 and 17. Preferably, the resistance members are coupled one toward each side on the anterior of the belt as it is on the user. As such, the resistance members coupled to the belt allow the user to self apply overpressure into the user's body to select regions on the user's back.

Resistance members can have an effective length between about 6 inches to about 36 inches long, for example, about 8, about 10, about 12, about 14, about 16, about 18, about 20, about 22, about 24, about 26, about 28, about 30, about 32, about 34, or about 36 inches in length. As used herein, the term "effective length" in reference to a resistance member means the length from the end of the band or tubing that is coupled to the belt to the other end (including the handle). In general, the effective length should not be so long that a user grasping the handles of the resistance members is unable to stretch the bands or tubings by extending the user's arms when the members are coupled to the belt fastened around the user's lumbar region. In addition, the effective length of the resistance bands or tubings should not be so short that even where they are stretched to their fullest, the user grasping the handles of the bands or tubings is unable to fully extending the user's arms in a direction away from the belt. Resistance members can have any convenient length that allows the user to performed resistance exercises by stretching the resistance members attached to the belt.

Resistance bands or tubings are generally known to those of skill in the art. Resistance bands or tubings are constructed of a flexible, elastic material such as latex or synthetic rubber and can include a snap prevention material such as an inner braided cord having a length three to five times the length of the resistance band or tubing. The resistance band or tubing can have any convenient size and tension level.

The handle at one end of the resistance member can be made of the same material as the resistance band or tubing, or it can be made of a different material than the resistance band or tubing. For example, the end of a resistance band or tubing can be clipped with a flat band clip that itself can function as a handle, or an end portion of the resistance band or tubing can be turned toward and secured to another region of the resistance band or tubing, respectively, to form a loop. The portions that come together to form the loop can be secured using any means known to those of skill in the art including, without limitation, tying or knotting together of the resistance band or tubing portions, clamping or clipping of the portions using a metal or/and plastic clamp, clip or spring-loaded locking mechanism, or binding the portions together with a wire or non-wire binder. The loop so formed can be used as a handle for gripping.

Figure 10:
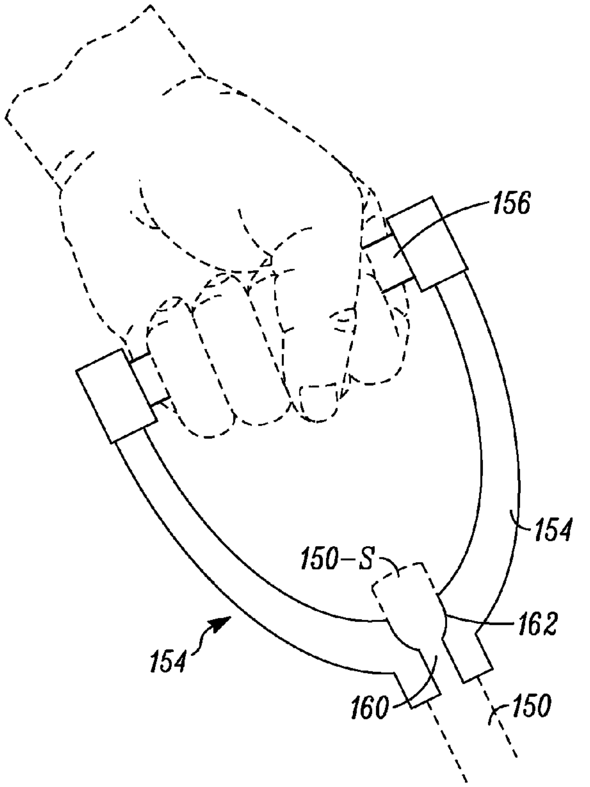
FIG. 10 is an illustration of a rigid handle to which a resistance band or tubing can be detachably secured.

The loop formed by the end portion of the resistance band or tubing can also function as a connecting means from which a separate and distinct handle can be attached. Thus, the handle can be a distinct component detachably connected to the end of the resistance band or tubing using any connectors known to those of skill in the art. For example, the handle can be made of foam, cotton, flax, nylon, polypropylene, polyester, Dyneema or Kevlar webbing detachably connected to the resistance band or tubing through a ring, clip or snap, or a combination of a ring and a clip or snap. For example, the end portions of an elongated, flexible webbing can be stitched or otherwise joined together to form a loop that can function as a handle. The elongated webbing can be threaded through a connector such as a ring, clip or snap prior to being joined at the ends to form the loop, or the connector can be secured to the handle using any means known to those of skill in the art including stitching. The resulting handle can be linked to the loop at the end of the resistance band or tubing through a split ring, or it can be clipped to the loop at the end of the band or tubing as discussed above or clipped to a ring attached to the end of the band or tubing using a clip or snap. Alternatively, the handle can have a rigid frame with a gripping pin for the user's hands as described in U.S. Pat. No. 6,923,750. For example, the rigid frame can include a base having a slot and cradle through which a resistance band or tubing can be inserted (FIGS. 10 & 11). In these embodiments, to prevent detachment from the handle after the resistance band or tubing is inserted through the slot in the handle, the resistance band or tubing can be configured with a stop at its end that is wider than the slot in the rigid frame, or the band or tubing can be knotted at the end of the resistance band or tubing after it is inserted through the opening.

In some embodiments, the handle can include a rigid or semi-rigid bar to assist the user with grip. Where the handle is a loop formed by the end portion of the resistance band or tubing, or a loop made of flexible webbing, a section of the loop can be encased in or otherwise secured to a rigid and/or semi-rigid material thereby forming a handle bar to facilitate grip. The handle bar can be a cylinder with a central opening to accommodate a section of the loop. The handle bar can further include semi-rigid foam covering on its surface for increase comfort. In these embodiments, the resistance band, tubing or flexible webbing can be inserted through the opening in the rigid or semi-rigid handle bar before forming the handle loop or the rigid or semi-rigid handle can include a narrow longitudinal slit through which a section of the band, tubing or webbing of the loop can be inserted thereby allowing the handled to be affixed to a section of the loop after the loop is formed.

The resistance members can be coupled to the belt using any means known to those of skill in the art. The resistance member can be directly coupled to the belt by forming a loop on one end that allows the resistance member to hang from the belt. For example, one end portion of the resistance band or tubing can be inserted behind a section of the belt then folded over the belt to form a loop transversely encircling a section of the belt. Alternatively, a loop can be formed at the end of the resistance band or loop, and the belt can be inserted through the loop. The loop can be maintained using any means known to those of skill in the art including, without limitation, tying or knotting an end portion of the band or tubing to another portion of the band or tubing or using a clamp, clip, wire or non-wire binding, or spring-loaded locking mechanism such as one described in FIG. 9.

The resistance members can be indirectly coupled to the belt through one or more connectors that, optionally, allow the resistance members to be conveniently attached to or detached from the belt as needed. The one or more connector can have a rigid or flexible structure made of the same or different material than the belt or resistance members. The one or more connectors can be made of natural or synthetic leather, suede, canvas, cotton, flex, natural or synthetic rubber, plastic, nylon, polyvinyl chloride, polyester, polypropylene, other natural or synthetic fabric, polymer, plastic or webbing, one or more metal, an alloy such as steel or any combination thereof. The one or more connectors can include, without limitation, a split ring or closed ring that are round, oval, triangular, square, rectangular, or D-shape or that have any convenient symmetrical or asymmetrical shape; a flexible loop; a quick link or connecting link; a wire lever clip, carabiner clip, Bimini clip, harness clip or spring clip with or without slide lock, screw lock, auto lock or key lock; spring gate snap, trigger snap, bolt snap, wire lever snap or a snap shackle, with or without a fixed or swivel eye or bail; a utility hook, pelican hook with slide or slip hook with or without fixed or swivel eye; or a combination thereof.

A connector such as any ring, clip, snap or hook, for example, can form a link between the loop at one end of the resistance member and the belt from which it hangs. For example, a ring, clip, snap or hook of any shape, or a flexible loop, having an opening wide enough to accommodate the width of the belt can allow the belt to be inserted through the opening. In these embodiments, the connector hangs from the belt allowing a resistance member to be coupled to the belt by being clipped to the connector, or alternatively, allowing the resistance member to hang directly from the connector. In the latter case, the opening of the connector can be wide enough to accommodate the belt and the resistance member, thereby forming a small link between the belt and the resistance member. The connector can also hang from any structure on the belt such as one or more tabs stitched to selected positions along each side of the belt or one or more holes placed at selected positions along each side of the belt and to which a resistance remember can be clipped or linked.

The connector can be secured to the end of the resistance member using any means known to those of skill in the art. A connector having a central opening, an eye, bail or shackle such as that in a ring, clip or snap can be secured to the resistance member by insertion of the resistance member through the opening, eye, bail or shackle and then securing a portion of the inserted section to a portion of the un-inserted section together to form a loop. Alternatively, a second connector such as that shown in FIG. 8B can be used to facilitate coupling of the resistance member to the belt. In these embodiments, the end of the resistance member can include a stop that prevents separation of the resistance member from the connector with a reinforced opening through which the end of the resistance member has been inserted.

Uses for a Spinal Therapy Device of the Invention

The spinal therapy device can be used by an individual to self apply overpressure, decompression, joint mobilization, or any combination thereof to the lower back. The device allows the individual to address the exact spinal segment where end range of motion is desired. The device eliminates the need for a trained professional to provide skilled manual therapy techniques and allows the user to receive overpressure, decompression, joint mobilization or a combination thereof multiple times a day rather than two to three times a week where a professional therapist is needed.

Overpressure involves applying generally constant pressure in a directional force about 90° or perpendicular to the spine directed in a posterior-to-anterior direction or back to front. Overpressure promotes increase range of motion into an extended position at a specific spinal segment. This allows the spine to be manipulated into the full end range of motion and in some cases, beyond normal range. Spinal decompression involves applying a directional force into the spine directed toward the individual's feet, for example, in a direction about parallel or linear to the spine, causing the spinal segments to distract. As the vertebral bodies are pulled apart from one another, a gap is formed relieving pressure on the discs and the sinuvertebral nerves (pain nerves in the disc). Then as the decompression is released, the discs can return to a more natural position, thereby correcting disc bulge and discogenic problem. Decompression also stretches the muscles and soft tissue thereby reducing muscle spasm and muscle guarding and promoting proper alignment. Spinal joint mobilization involves applying small oscillation of pressure to the lumbar spine in a posterior to anterior direction to decrease pain and joint restrictions. The gentle, oscillatory passive movement is directed to a spinal region or segment to promote increase passive range of motion in that region or segment. Joint mobilization can involve small amplitude rhythmic oscillations at the beginning of the segment's range (Grade I), or larger amplitudes oscillations within the range of the segment (Grade II), both of which can be used to address joint pain by promoting musculature relaxation and joint lubrication. Joint mobilization can also involve larger amplitude oscillations within the segment's range to its end range of motion while stressing tissue resistance (Grade III), or small amplitude oscillations at the segment's end range of motion and stress into the tissue resistance (Grade IV), which also can be used to address joint pain, as well as increase joint play or range of motion. Spinal joint mobilization promotes end range of motion, joint lubrication, joint nutrition, and pain relief.

A device of the invention can be used by an individual to self apply overpressure, spinal decompression and/or spinal joint mobilization in various positions including in a standing, prone or supine position or in variations of these positions. A device of the invention can be used to self-apply overpressure, spinal decompression and/or joint mobilization through a series of exercise progressions such as that in accordance with the McKenzie method. A device of the invention can be employed in a standing position or in a prone position where the spine is unloaded, the pressure within the disc is decreased and the spine is in an extended position. The usability of a device of the invention in a prone position is particularly beneficial because as the spine extends backwards, the posterior aspect of the boney vertebral bodies compresses the posterior aspect of the disc thus moving the nucleus pulposus back into its original position and shifting the axial load anterior. A device of the invention can also be used in a prone on elbows or prone press-up position, the prone on elbows position allowing for greater extension to the lumbar spine, while the prone press-up position allowing the spine to move even further into an extended position. Use of a device of the invention in a standing back bend provides the same biomechanical benefits as that of the prone positions though in an axial loaded position.

To use a device of the invention, the user securely fastens the belt around the lumbar region positioning the belt at the desired spinal segment for therapy. Resistance members having the desired resistance can be coupled to the belt as described herein, for example, through two cloth or metal loops so that they can be easily positioned at any position on the belt. Where desired, resistance members are placed at the lateral aspect of the user's trunk, and their lengths adjusted, for example, using the resistance adjuster as needed or appropriate for the user. The anchor strap can be independently coupled to the belt as described herein, its length adjusted to extend from belt to the user's foot allowing the user's foot to engage with the anchor member to create a downward pressure on the belt.

Figure 14B:
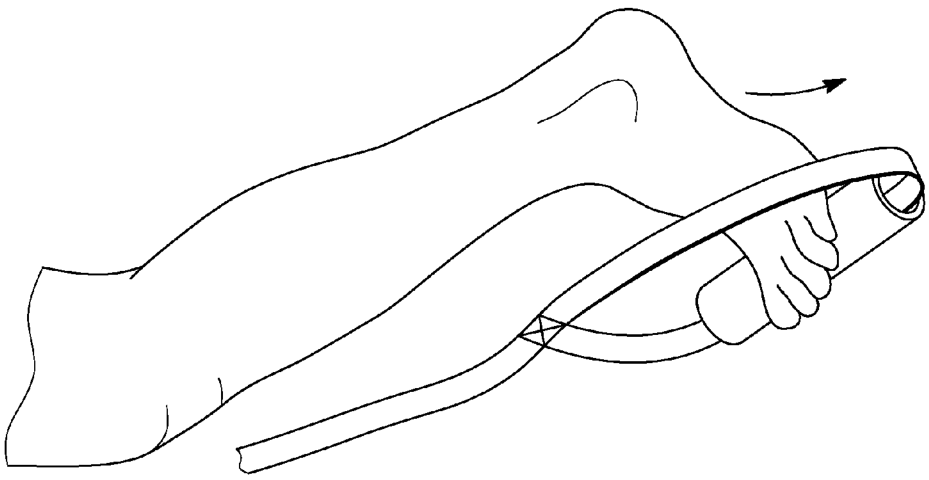
FIG. 14A-B illustrate the engagement of the user's foot with the anchor member to assist in maintaining the position of the lumbar belt and plantar flexing of the foot to allow for anchor-strap-mediated spinal decompression.
Figure 14A:
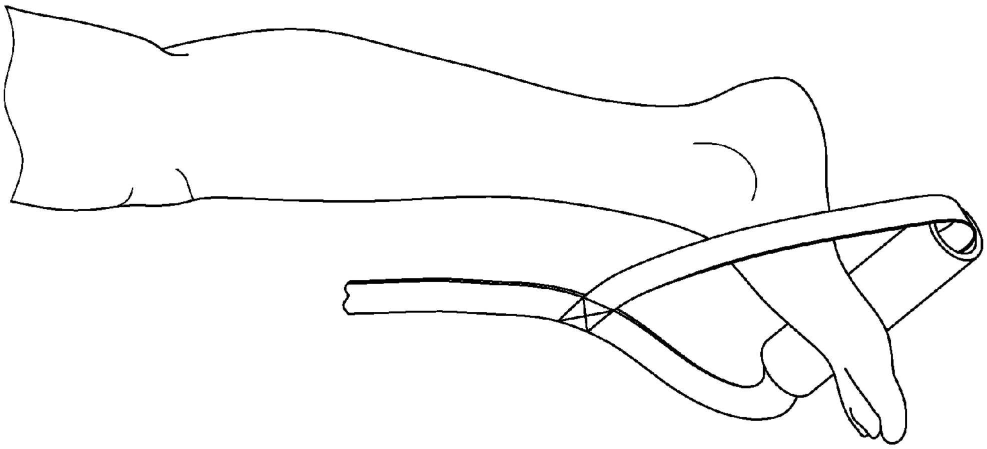

The anchor strap of a device of the invention allows the user to apply spinal decompression through the user's foot. For example, to perform spinal decompression exercises, the user can lay in a prone position, thereby moving the spine from a vertical position to a horizontal position causing the spine to be unloaded. The user's foot then engages with the anchor member on the anchor strap, for example, by insertion into an anchor loop as shown in FIG. 14A. As the anchor strap is coupled to a lumbar belt worn around the user and adjusted so that its length extends from the belt to the user's foot, by engaging the anchor member with the foot, the user can apply a directional force away from the pelvis and towards the user's feet thereby providing the initial decompression. The user can point her toes or plantar flex the foot engaged with the anchor member as shown in FIG. 14B to generate more distraction or spinal unloading at the desired spinal segment so as to achieve more decompression on the spine as needed. The amount of decompression can be controlled by the amount of planter flexion performed at the ankle. Increasing the plantar flexion increases the force of decompression. The spinal decompression allows for mechanical decompression of the disc and sinuvertebral nerves. By performing decompression in a prone position, more tension can be placed on the anchor strap. Decompression can also be preformed in a standing position.

Figure 15A:
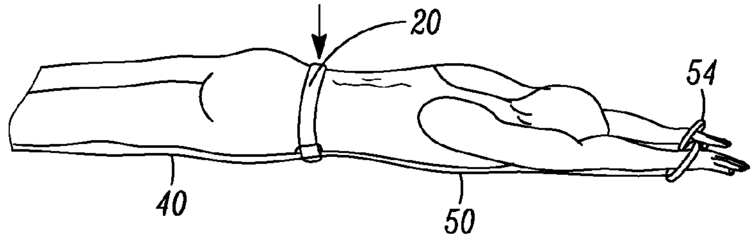
FIG. 15A-D illustrate use of a spinal therapy device of the invention in a prone, prone on elbows, press up or supine with knee-to-chest position, respectively, to achieve decompression and/or overpressure.

A device of the invention can be used to self-apply overpressure to the spine. Overpressure can be applied as the user adopts various positions including supine, prone, prone on elbows, prone press up, or during exercise progression. The exercises are most efficient when the spinal segment moves to its furthest end range of motion into extension to promote the most amount of healing. To apply overpressure to the spine, the user can lie in a prone position, with the foot engaging the anchor member and the hands gripping the handles of the resistive members. In this position, spinal decompression is applied to the spine through the user's foot engaging with the anchor strap as discussed above. The user then extends her arms reaching above her head and extending the resistant members as shown in FIG. 15A. In doing so, two opposing directional forces, a superior force and inferior force, are created at the desire segment. The opposing forces result in a distraction at the spinal segment and a net directional force into the spine at about 90° in a posterior to anterior direction thereby creating overpressure at the spine. The overpressure and distraction allow for the disc to begin shifting its axial load anterior, causing it to mechanically unload the sinuvertebral nerves thus decreasing pain.

Figure 15B:
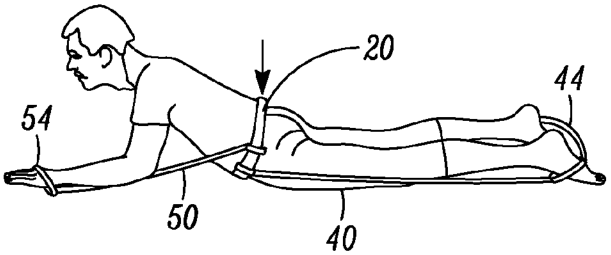
Figure 15C:
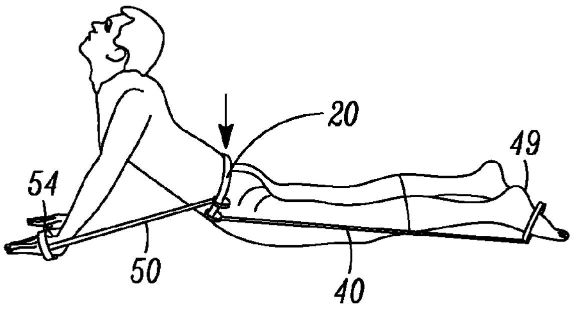

Similar directional forces are achieved as the user adopts a prone on elbow position or a push up position. The user can transition into a prone position on elbows to move the spine into an extended position as shown in FIG. 15B. As the spine extends, the disc's axial load is shifted to a more anterior position. With the distraction and unloading of the spinal segments, the posterior aspect of the disc is more easily compressed and less pain occurs with the extension of the spine. The overpressure allows the spine to extend at the exact segment and pushes the spine further into extension. Use of a device of the invention in these exercises allows the user to achieve closer end range of motion of the spine. Additional decompression and/or overpressure can be applied as the user adopts a push up position. The user can move her hands into a push up position, perform a push up, and then allow the pelvis to hang towards the floor as shown in FIG. 15C. This allows for an even greater amount of extension at the desired spinal segment. As with the prone position, the spinal segment is distracted or decompressed. The decompression relieves the pressure on the disc, allowing the exercises to become more tolerable. Overpressure is simultaneously applied and the segment can move into or beyond the individual's end range of motion. For users who find it difficult to relax their musculature or have increased muscle tone and/or guarding surrounding the desired spinal segment, the device of the invention facilitates relaxation of the musculature surrounding the segment and allows individuals who "hinge" at another level to achieve the desired end range of motion at the targeted spinal level. For users who may benefit posterior lateral compression on the disc, the user can offset the shoulders and hips to the same side moving through the above described exercise progression with a posterior lateral overpressure.

Figure 15D:
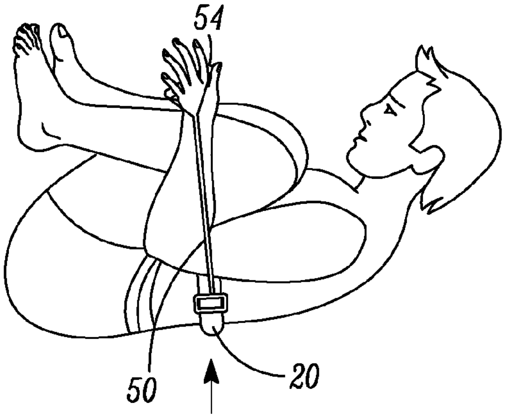

A device of the invention can also be used in a supine position as illustrated in FIG. 15D. In this embodiment, the lumbar belt is fastened around the lumbar region of the user at the level of the dysfunction. The user lies supine bringing knees to chest, grips the resistance bands with her hands and reaching upwards to wrap her hands around her knees thereby extending the resistance bands and exerting a force upward from a posterior to anterior direction into the back. A device of the invention can also be used in similar flexion exercises in which the user is in a seated or supine position. In this case, the user brings one or both knees to her chest and extends the resistance members by wrapping the users hands around one or both knees.

Figure 16B:
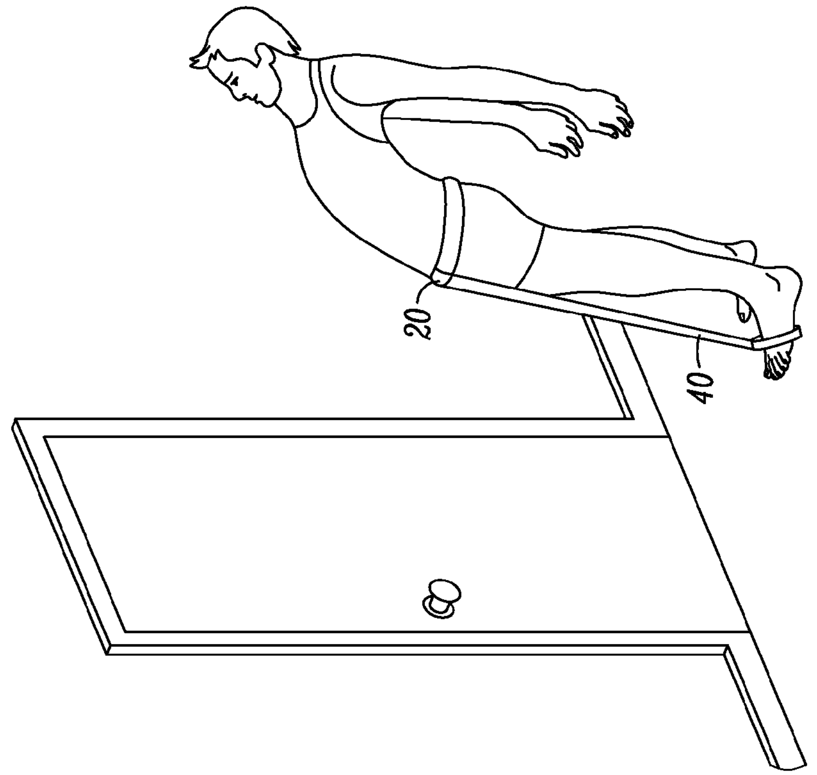
FIG. 16A-B illustrate use of a spinal therapy device of the invention for standing extensions with overpressure to spine.
Figure 16A:
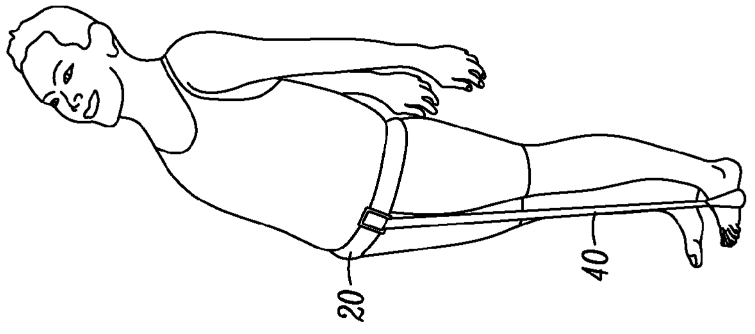
Figure 17B:
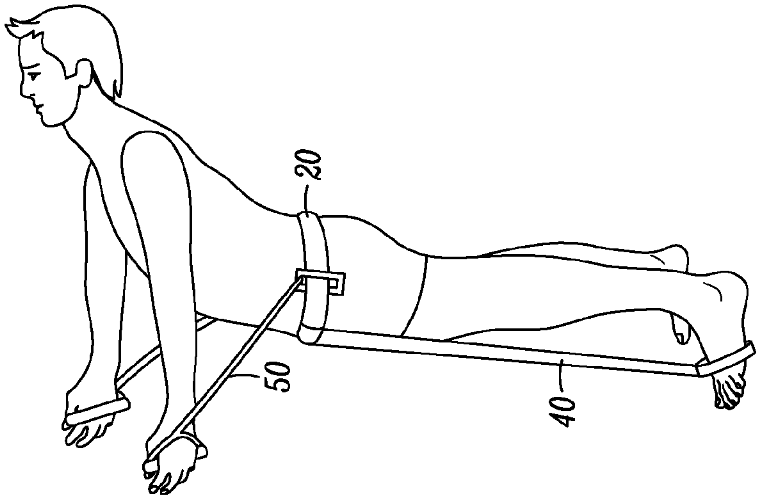
FIG. 17A-B illustrate use of a spinal therapy device of the invention for standing extensions with overpressure to spine.
Figure 17A:
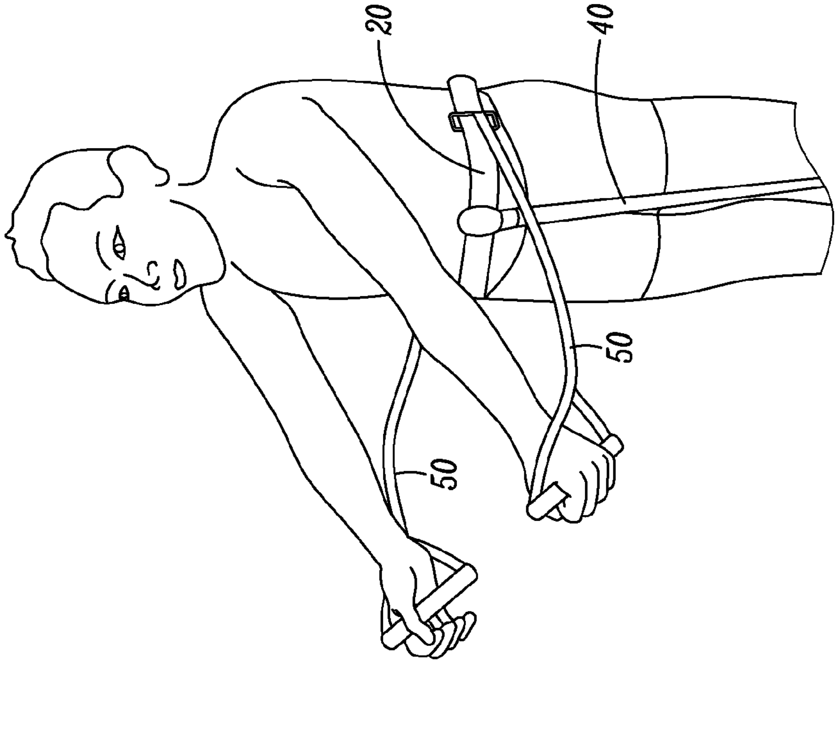
Figure 18A:
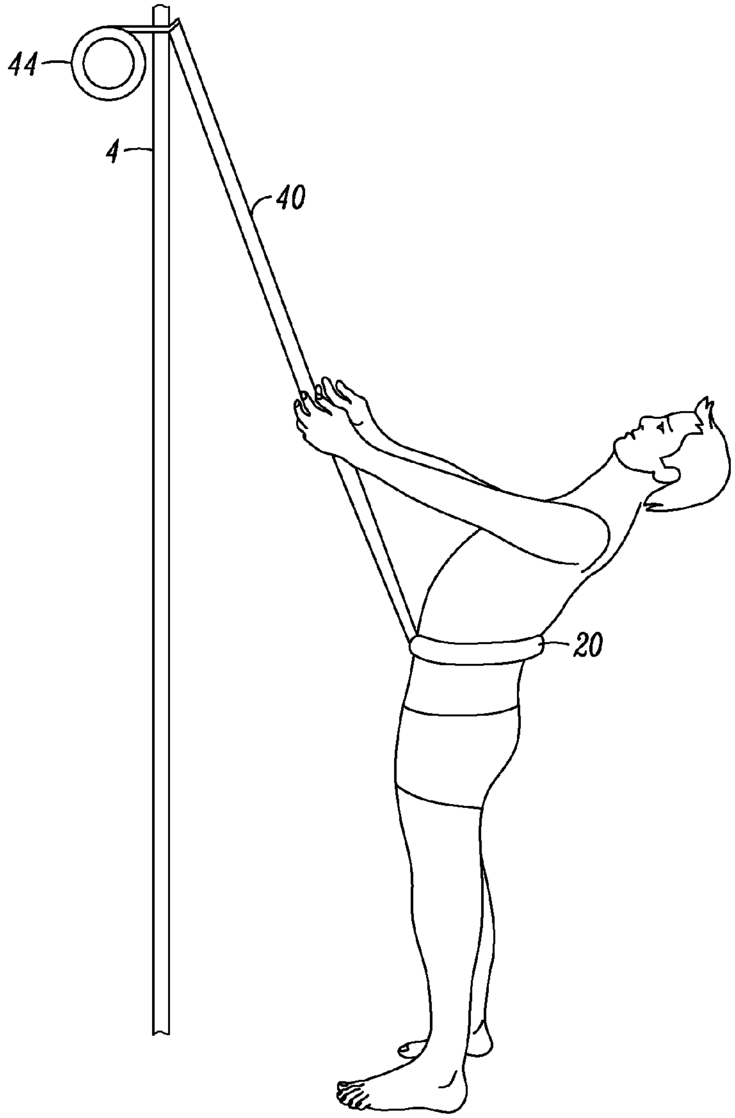
FIG. 18A-B illustrate use of a belt and coupled anchor strap to perform a standing backbend (A), the anchor strap being secured between the door and frame (B).
Figure 18B:
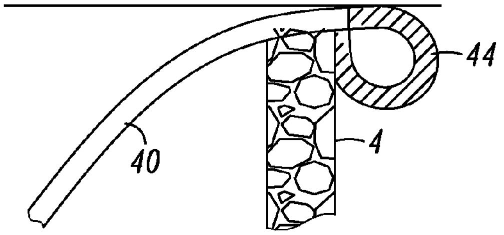

A device of the invention can also be used in a standing position as shown in FIG. 16-18 to self-apply decompression and/or overpressure. As described above, the lumbar belt can be fastened around the lumbar region of the user at a selected spinal segment and maintained in position by the user's foot engaging with the anchor member of the anchor strap as illustrated in FIGS. 16 and 17. Overpressure can be applied by extending backwards over the lumbar belt as shown in FIGS. 16A and 16B. Overpressure can be applied through the coupled resistance bands as shown in FIGS. 17A and 17B or through the coupled anchor strap as shown in FIG. 18A. The anchor strap can be secured between the frame and top of a closed door as shown in FIG. 18B or in a similar manner between frame and side of a closed door. In these embodiments, the anchor member can function to securely anchor the strap between the closed door and doorframe. The user may self-apply overpressure to a selected spinal segment by leaning backwards or performing a back bend. By holding onto the anchor strap, the musculature around the spine can relax, thereby combating muscle tone and muscle guarding and increasing the effectiveness of a traditional back bend exercise. In some embodiments, the user can employ an anchor strap of the invention with a general use belt to self-administer decompression and/or overpressure as described.

Figure 13A:
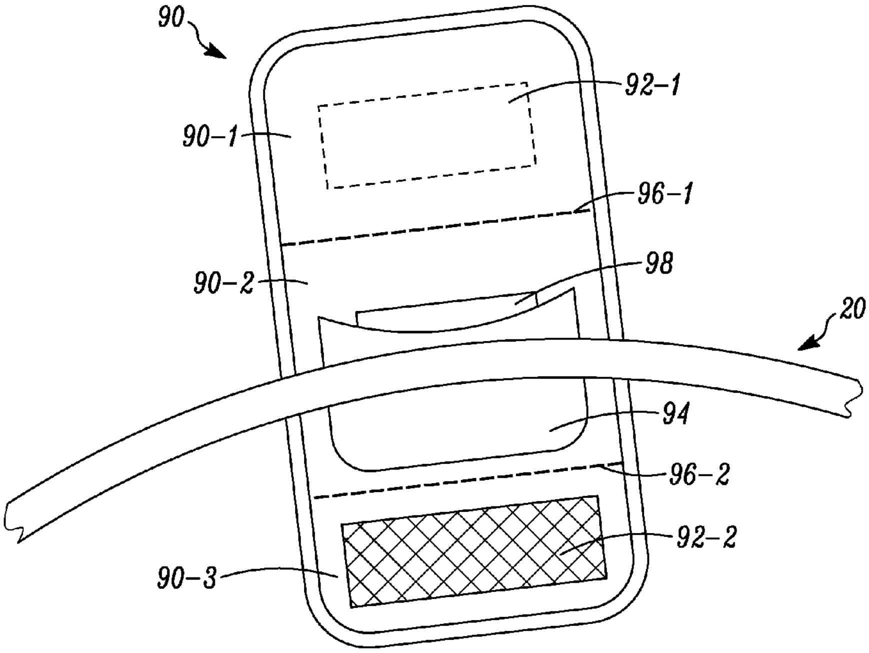
FIG. 13A-B are interior and exterior perspective views, respectively, of a detachable pouch for coupling a therapeutic device with a device of the invention.
Figure 13B:
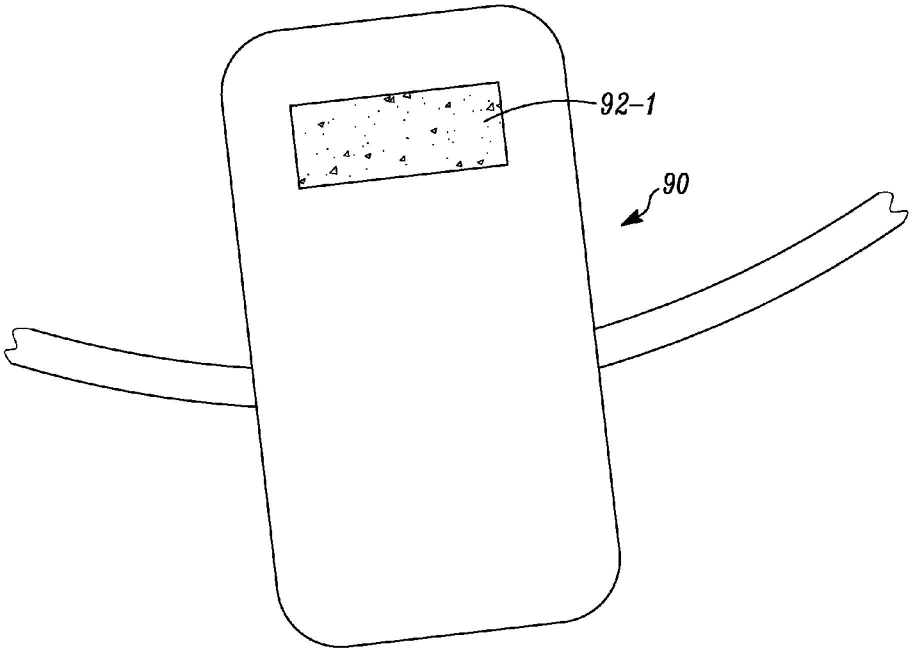

A device of the invention can be used in combination with another therapeutic component such as a hot or cold pack, a vibration device, acupressure/mobilizer ball or the like. For example, to achieve joint mobilization to the spine, a joint mobilizer consisting of a small mechanical vibrating device similar to the ones in cellular phones can be used. The vibrating device can be located inside a cloth pouch that can be coupled to a lumbar belt as shown in FIG. 13. The lumbar belt with pouch and vibrating device can be placed at a selected segment on the spine. While performing the exercise progression, the individual may turn on the vibrating device via a switch or remote, thereby creating large and small oscillations to the spine. This provides Grade I-IV spinal joint mobilizations to the spine, which allow for pain reduction and increase range of motion without assistance from a clinician.

A device of the invention can also be used with a hot/cold pack. Cold application vasoconstricts the blood vessels and allows for a decrease in the inflammatory response, which is most called for in the acute and subacute phases of the healing process. Cold application also decreases nerve signals allowing pain to be perceived less thereby allowing for muscle relaxation and decreased muscle guarding. Heat vasodilates the blood vessels causing increased blood flow to an area. Heat treatment is most appropriate in the subacute and chronic phase of the healing process. It increases fluid into an injured area allowing for old static fluid to be removed and providing healing nutrients to enter the injured area. Heat also promotes soft tissue extensibility and muscle relaxation thereby helping to combat muscle guarding and spasms. For hot or cold application, a common hot/cold pack can be inserted into a pouch, which can be attached to the primary belt. The hot or cold pack can be applied in conjunction with the joint mobilizer as the pouch fits around the joint mobilizer apparatus. This allows the individual to use the benefits of heat and cold while performing the exercise progression. Thus, by coupling a vibrating device to the lumbar belt, the user of a device of the invention can self-applied joint mobilization in a variety of exercise positions as discussed above including, for example, in a static prone position (while lying on the stomach without motion at the spine), in a press-up position, while performing the exercise progression or in a standing position as shown in FIG. 19.

Where a device of the invention is used with an acupressure/mobilizer ball, the ball attachment can be placed on a specific low back muscle such as the paraspinals or quadratus lumborum so that when the user lies on the acupressure ball, and the weight of the body and the density of the ball allows the musculature to relax underneath, thereby decreasing tone, muscle guarding and muscle spasm. The ball attachment can also be placed on the transverse processes or lateral portion of the spine to assist in mobilizing the vertebrae into the correct alignment during rotational exercises. The attachment may also be used to help posterior torsions in the sacral iliac joint by placing the attachment on the illium and lying supine on the attachment.

A device of the invention can also be used for a series of exercises to stretch and strengthen the core known to those of skill in the art. With the anchor strap securely latched onto the belt and the resistance members placed appropriately along the belt, isometric core stabilization exercises can be performed by moving one's arms while stabilizing the trunk. Further, resistance exercises beneficial to the core can be performed by attaching the resistance members to static objects and moving the trunk. The strengthening exercises target the paraspinals, quadratus lumborum, rectus and transverse abdominals, the pelvic floor and any other muscles within the core known within the art. Illiotibial band, piriformis and hamstring stretches may be performed in a supine position and/or standing position using the anchor strap thereby enabling preventative care.

Figure 20:
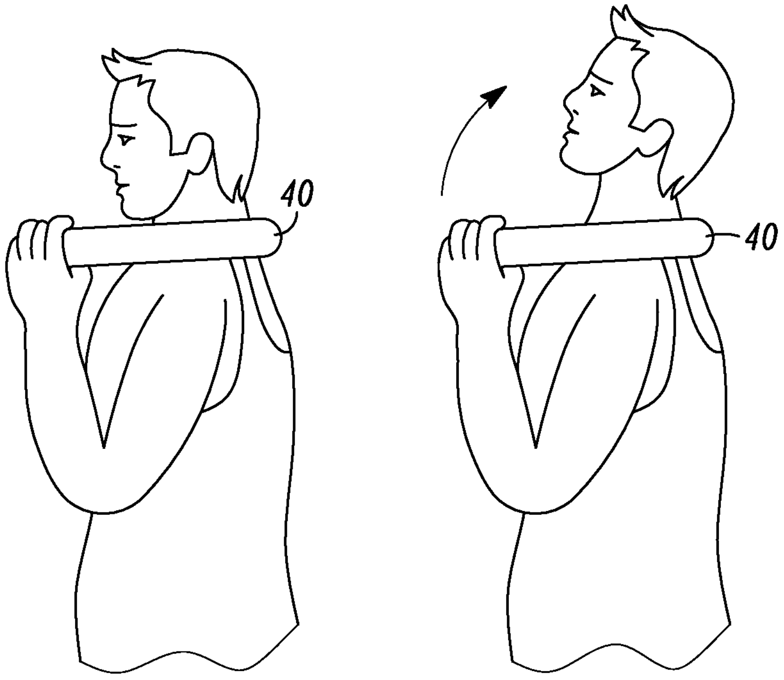
FIG. 20 illustrate use of an anchor strap of the invention by an individual in a cervical spine exercise.

The anchor strap can also be used towards a series of cervical spine exercises. More specifically, two loops can be formed at each end of the anchor strap to form handles. The foot loop can serve as the first handle, while adjusting the Velcro forms a loop that function as a second handle. The anchor strap can be placed on the desired cervical spine level with the individual's hands within the two loops, for example as shown in FIG. 20. A retraction exercise can be performed while the individual's hands provide an equal but, opposite directional force on the anchor strap 40 (see FIG. 20). This causes inferior vertebrae to remain in a static or anterior position, allowing the superior vertebrae to move in a posterior direction. In the cervical spine this causes an axial load shift anterior, decreasing cervical spine discogenic pain. Side bend and rotation exercises can also be performed as motion is isolated segmentally by the device of the invention. The cervical spine exercises follow both the McKenzie method and the Mulligan theory of treatment as known to those of skill in the art.

Thus, a device of the invention, including lumbar belt, anchor strap and/or resistance bands can be used to self-apply decompression, overpressure, joint mobilization, or a combination of these therapies, as well as other cervical spine exercises or core strengthening exercises as desired as needed or as the user is able.

Specific embodiments of the invention are described in the following examples, which do not limit the scope of the invention described in the claims.

Examples

An embodiment of a spinal therapy device of the invention is illustrated in FIG. 1. In this embodiment, the spinal therapy device 10 includes belt 20, anchor strap 40 and two resistance members 50. First end portion 20-1 of belt 20 is shown terminating with belt fastening ring 22, which can be a square-, rectangular-, circular- or D-ring. The second end portion 20-2 of belt 20 is constructed with hook and loop fasteners on exterior side 20E of belt 20. The hook and loop fasteners include complementary members placed in series that adhere when pressed together. The complementary hook and loop fastener members are placed in series along exterior side 20E at second end portion 20-2 of the belt. To fasten belt 20 around the user, second end portion 20-2 is passed through ring 22, then folded back on itself bringing the complementary hook and loop fastener members on exterior side 20E together thereby securing belt 20 around the user. Belt 20 is also threaded though two resistance member connector 30, which are independently slidable along the length of belt 20.

Figure 4A:
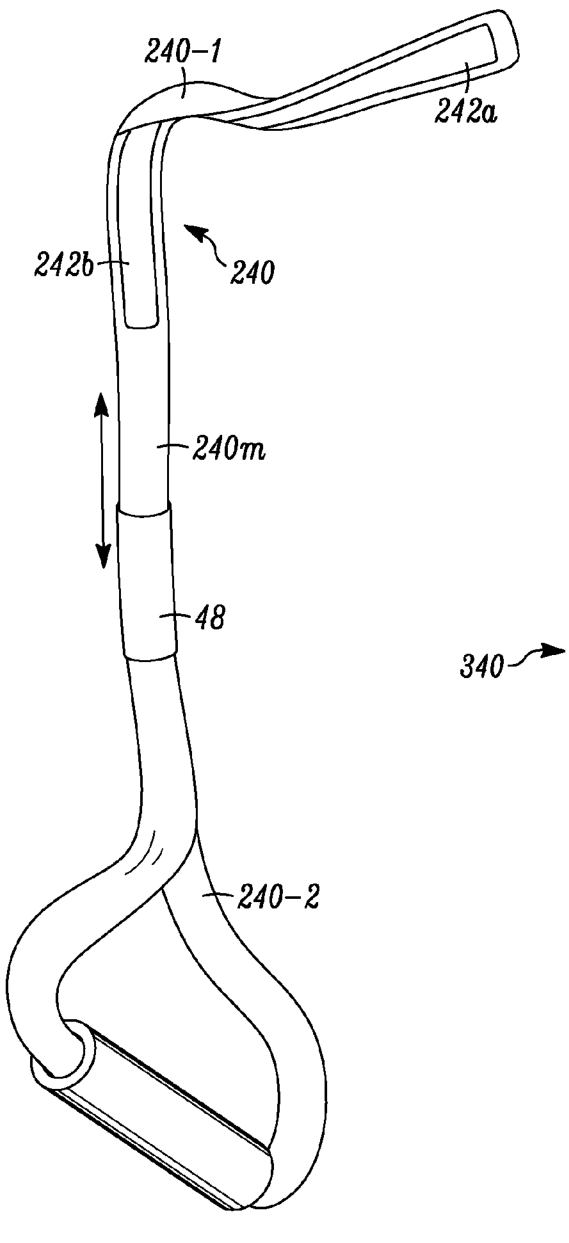
FIG. 4A-B are perspective views of two adjustable-length anchor straps, anchor strap 240 having a hook and loop fastener at one end (4A) and anchor strap 340 having two segments connected by a quick-release buckle (4B), that can be used in a device of the invention.

Anchor strap 40 is removably coupled to belt 20 through belt fastening ring 22. First end portion 40-1 of anchor strap passes through ring 22 and is secured to mid-section 40M of the strap using complementary strips of hook and loop fasteners 42. Second end portion 40-2 of strap wraps back to form anchor loop 46 having handle bar 44. Anchor strap 40 can include slidable casing 48 (FIG. 4) in mid-section 40*m* of strap to facilitate grip, as well as to support the hook-and-loop-mediated attachment of the end of the anchor strap to main body portion of the anchor strap at first end portion 40-1. Slidable casing 48 can be moved up and down the length of main body section 40*m* as shown by the arrows.

Resistance member 50 is slidably coupled to belt 20 through resistance member connector 30. One end of resistance member 50 is threaded through connector with reinforced eyelet 34 secured to belt attachment clip 32. Belt clip 32 is clipped to resistance member connector 30, thereby slidably coupling resistance member 50 to belt 20. The other end of resistance member 50 loops back on itself to form loop 54 held in place by spring-loaded band lock 60. Lock 60 can be slidably secured to resistance member 50 at one or two points to allow for independent adjustment of the length of each resistance member (from attached end to free end), as well as the size of the loop formed. A segment of resistance member 50 that forms loop 54 is wrapped with plastic or foam to form handle bar 56 thereby facilitating grip. Components of a device of the invention shown in FIG. 1 are summarized below.

| | |
|---|---|
| Lumbar belt | 20 |
| Belt 1st end tab | 20-1 |
| Belt 2nd end portion | 20-2 |
| Belt exterior face | 20E |
| Belt inner-face | 20I |
| Belt fastening ring | 22 |
| Belt hook & loop fastener | 24 |
| Band connector | 30 |
| Anchor strap | 40 |
| 1st end portion of strap | 40-1 |
| Strap mid-section | 40M |
| 2nd end portion of strap | 40-2 |
| Hook & loop fastener | 42 |
| Anchor loop | 44 |
| Anchor loop grip | 46 |
| Slidable casing | 48 |
| Resistance member | 50 |
| Resistance member connector | 30 |
| Belt clip | 32 |
| Connector with reinforced eyelet | 34 |
| End bulge | 52 |
| Member loop | 54 |
| Band handle bar | 56 |
| Spring-loaded lock | 60 |

Figure 2A:
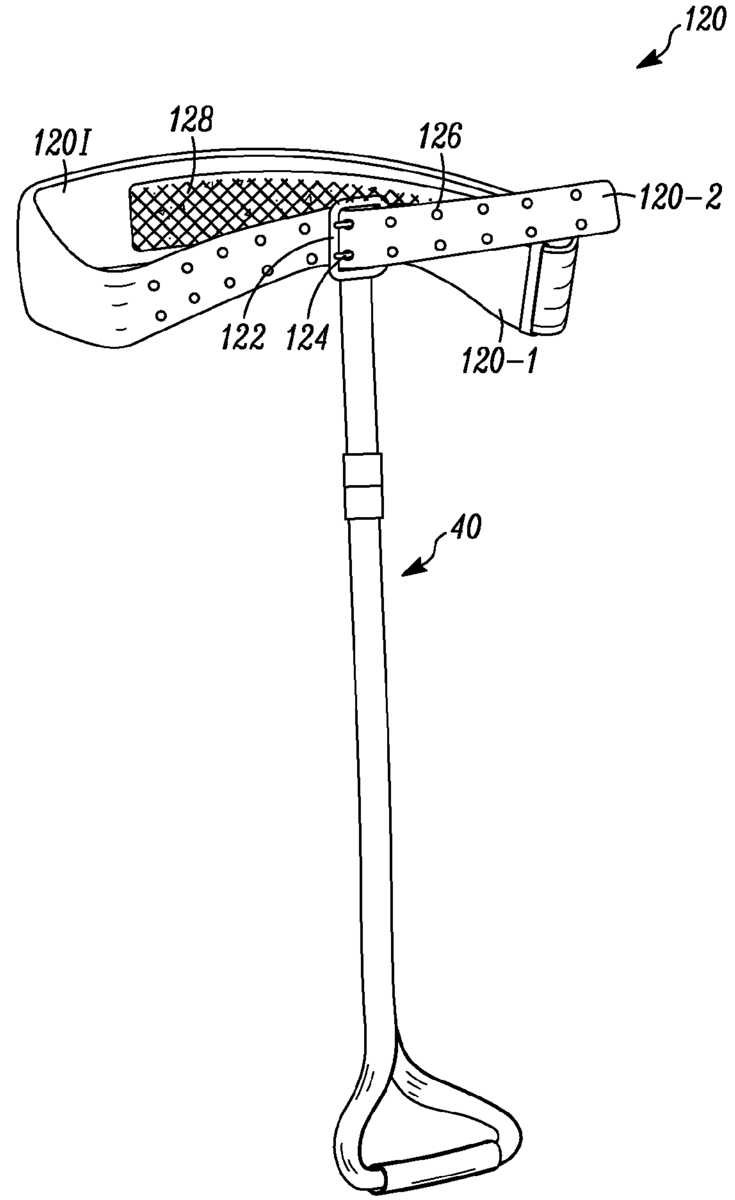
FIG. 2A-D are illustrations of belt fasteners that can be used to secure the effective ends of a belt in a device of the invention including a prong buckle (2A), a three-opening ring (2B), two-opening ring (2C) and a single-opening ring (2D).
Figure 2B:
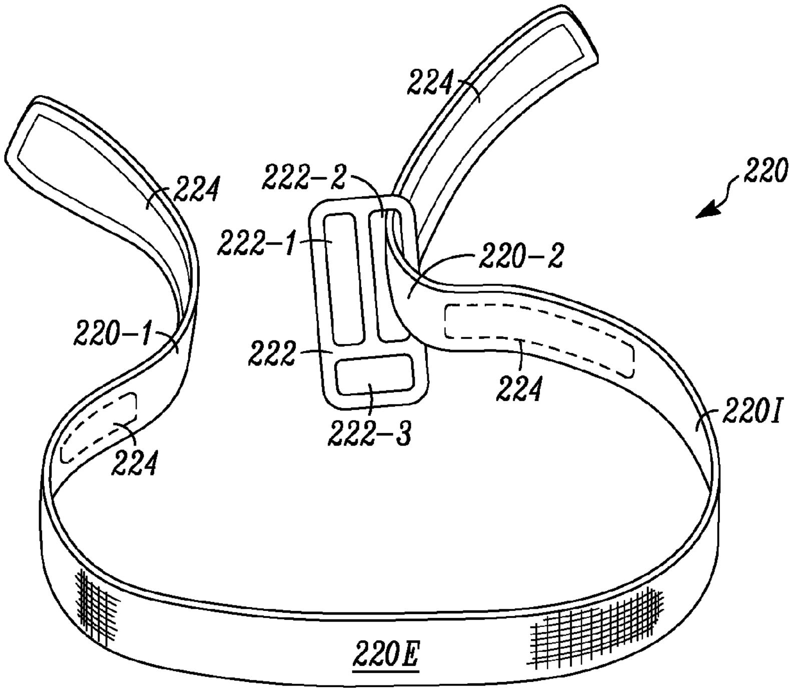
Figure 2C:
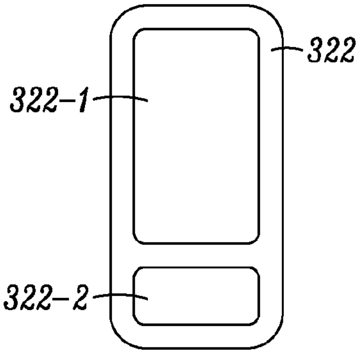
Figure 2D:
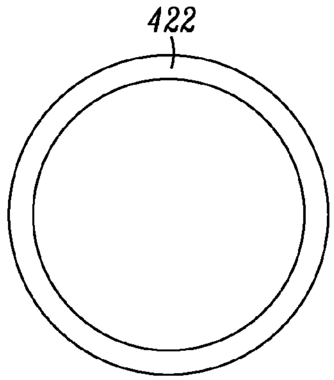

FIG. 2A-D show belts with different belt fastening assemblies. In FIG. 2A, the ends of belt 120 are fastened using a buckle mechanism. First end portion 120-1 of belt is secured to buckle 122, while second end portion 120-2 of belt is constructed with holes 126 to receive prong 124. Non-stick liner 128 is attached to a mid-posterior section on inner-face 120I of belt to minimizing sliding or shifting of the belt using use. In this embodiment, anchor strap 40 can be coupled to the belt by hanging directly from the buckle frame. In FIG. 2B, both end portions of the belt are constructed with hook and loop fasteners on the exterior face. Each end portion is inserted through one of two parallel slots of a three-slot buckle, then folded back and secured in place using the hook and loop fasteners. More specifically, first end portion 220-1 is inserted through slot 222-1 and then folded back on itself so that exterior, contiguous sections at first end portion 220-1 are opposing. These exterior sections adhere through hook and loop fasteners attached in series on the exterior face of belt 220. Similarly, second end portion 220-2 is inserted through slot 222-2, and then folded back on itself so that exterior, contiguous sections on second end portion 220-2 are opposing. The exterior opposing sections then adhere through hook and loop fasteners attached in series on the exterior face of belt 220. In these embodiments, the anchor strap can be coupled to the belt by hanging from lower slot 222-3. Having hook and loop fasteners on each end allow the user to continue tightening the belt on each side until the desired tightness is reached. FIGS. 2C and 2D show alternatives to the three-slot ring of FIG. 2B. Both first and second ends of the belt can be inserted through the slot 322-1 of ring 322 and then fastened using hook and look fasteners as described above for FIG. 2B. In this embodiment, the anchor strap can be inserted through bottom slot 322-2. Alternatively, both first and second ends of the belt, as well as the anchor strap can be inserted through the opening of circular ring 422 (FIG. 2D) or the square or rectangular ring 522 (FIG. 3). Components shown in FIG. 2 are summarized below.

| | |
|---|---|
| Belt | 120 |
| Belt 1st end tab | 120-1 |
| Belt 2nd end portion | 120-2 |
| Belt exterior face | 120E |
| Belt inner-face | 120I |
| Belt buckle | 122 |
| Buckle prong | 124 |
| Prong holes | 126 |
| Liner | 128 |
| Belt | 220 |
| 1st end portion | 220-1 |
| 2nd end portion | 220-2 |
| Belt exterior face | 220E |
| Belt inner-face | 220I |
| 3-slot ring | 222 |
| Belt 1st end slot | 222-1 |
| Belt 2nd end slot | 222-2 |
| Anchor strap slot | 222-3 |
| Hook & loop fastener | 224 |
| Two-slot ring | 322 |
| Belt slot | 322-1 |
| Anchor strap slot | 322-2 |
| Ring | 422 |

Figure 3A:
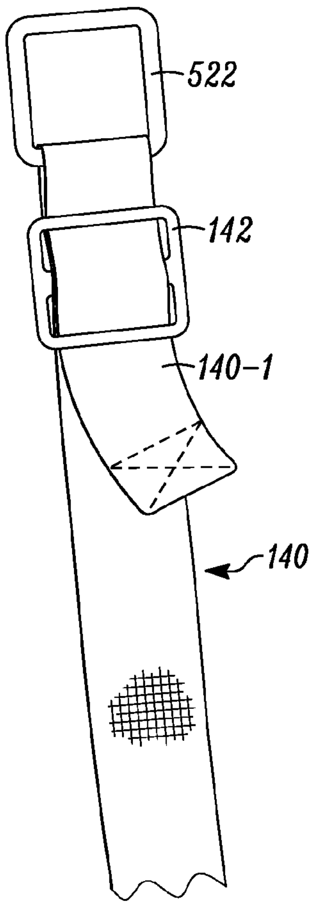
FIG. 3A-C are illustrations showing use of a fixed threading plate (3B) for adjustably securing together two portions of an anchor strap (3C) to form a loop allowing the anchor strap to be coupled to a belt (3A).
Figure 3B:
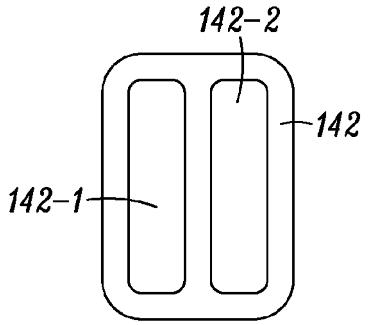
Figure 3C:
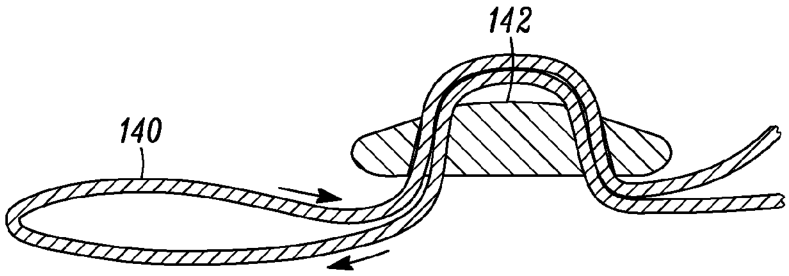

FIG. 3-6 show various embodiments of the anchor strap. In FIG. 3A, anchor strap 140 hangs from square or rectangular ring 522 and is held in place using fixed threading plate 142. Threading plate 142 includes slots 142-1 and 142-2 through which the anchor strap is inserted as shown by the arrows (FIG. 3C). By securing the end of the strap to main body region 140*m* using an adjustable slide or fixed threading plate 142 as shown, the effective length of the strap, i.e. distance from belt to free or loop end of strap, can be adjusted by increasing or decreasing the length of the leading portion, i.e. the portion of the strap that has passed through ring 522. By shortening the leading portion of the strap, the effective length of strap 140 increases. In contrast, by increasing the length of the leading portion of strap 140, the effective length of anchor strap 140 is shortened. FIG. 4A illustrates use of hook and loop fasteners 242*a* and 242*b* in place of the slide or threading plate of FIG. 3 for securing the leading portion to the main-body portion at first end 240-1 of anchor strap 240. The length of strap 240 is adjustable as described for FIG. 3. Strap 240 also includes slidable casing 48. Components shown in FIG. 3 are summarized below.

| | | | |
|---|---|---|---|
| Anchor strap | 140 | Anchor strap | 240 |
| 1st end portion | 140-1 | 1st end portion | 240-1 |
| 2nd end portion | 140-2 | 2nd end portion | 240-2 |
| Fixed threading plate | 142 | Hook & loop fasteners | 242a & b |
| Ring | 522 | Slidable casing | 248 |

Figure 4B:
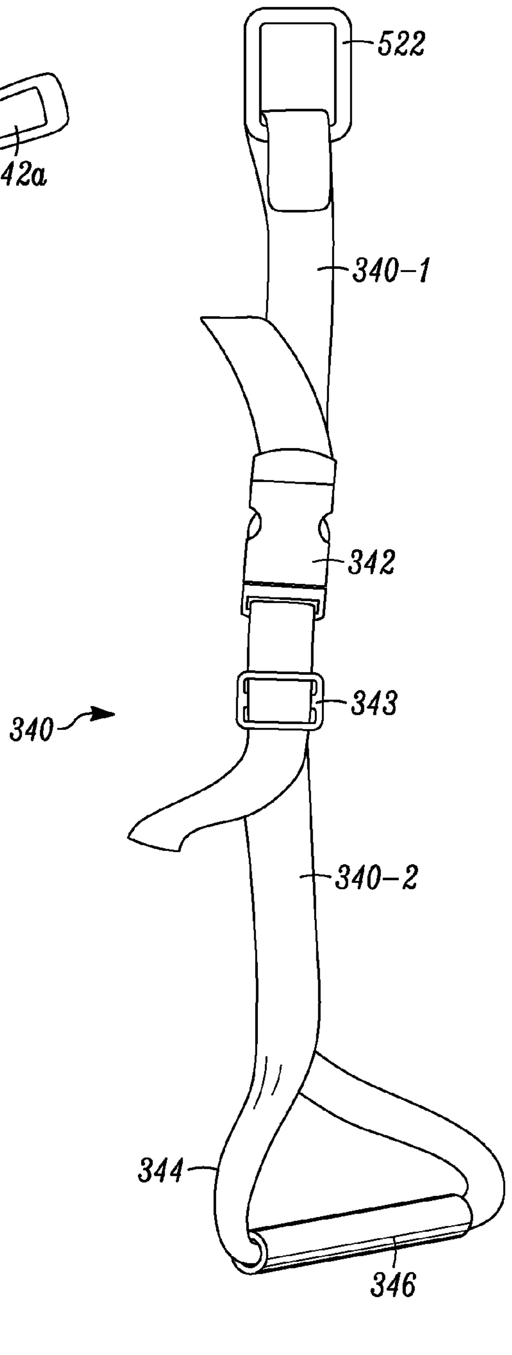
Figure 5A:
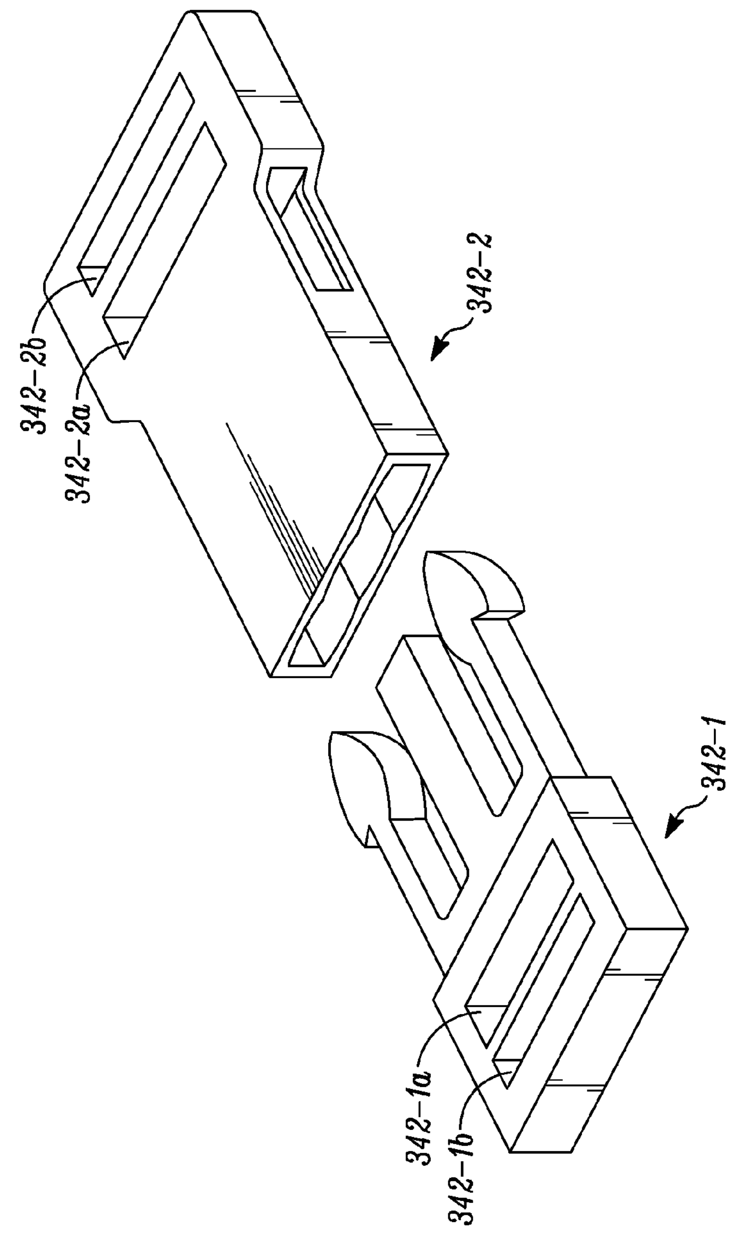
FIG. 5A-B are perspective and cross-sectional views, respectively, of quick-release buckle 340 illustrating how it secures together two portions of an length-adjustable anchor strap of FIG. 4B.
Figure 5B:
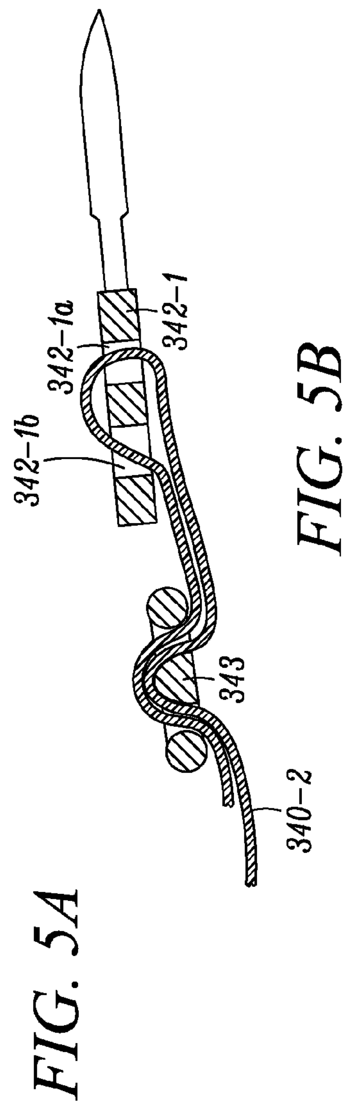

FIGS. 4B, 5 & 6 illustrate alternative embodiments of the anchor strap. In these embodiments, the anchor strap is composed of two segments joined by a connector. FIG. 4B depicts anchor strap 340 with first segment 340-1 and anchor segment 340-2 joined by quick-release buckle 342. One end of first segment 340-1 is coupled to a belt of the invention via square or rectangular ring 522, while the second end of first segment 340-1 attached to quick-release buckle 342. Similarly, one end of anchor segment 340-2 is secured to quick-release buckle 342, while the other end of anchor segment 340-2 terminates in anchor loop 344 with grip 346. FIG. 5A depicts the two members of the quick-release buckle 342, specifically, 342-1 and 342-2, with slots through which the strap segments are threaded and secured. FIG. 5B provides a cross-sectional view of how the end portion of strap segment 340-2 is threaded to through the slots of quick-release buckle member 342-1 and fixed threading plate 343.

Figure 6A:
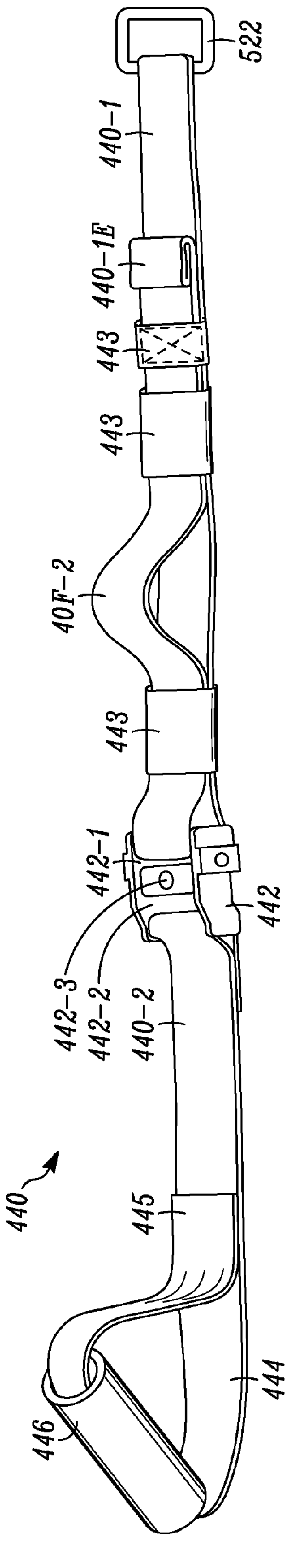
FIG. 6A-C are perspective views of a first embodiment of a length-adjustable anchor strap (FIG. 6A) and a second embodiment of a length adjustable anchor strap (FIG. 6B) composed of two anchor segments connected by cam buckle 442 that allows the length of the strap to be adjusted as shown in FIG. 6C.
Figure 6B:
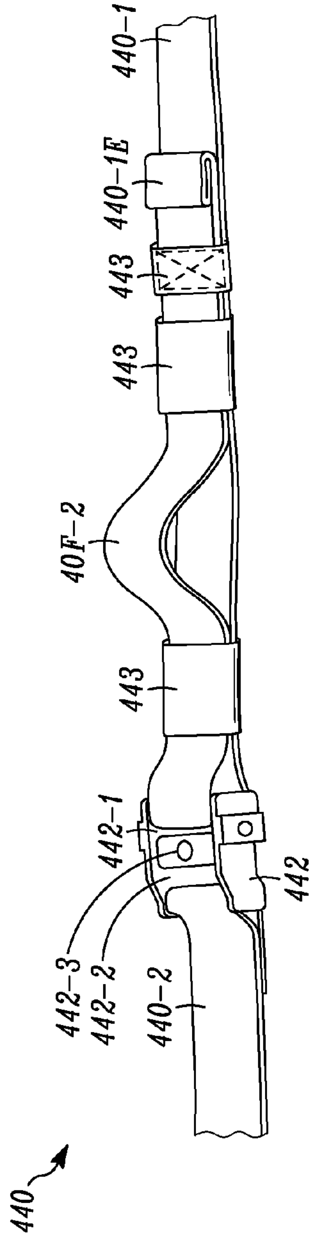
Figure 6C:
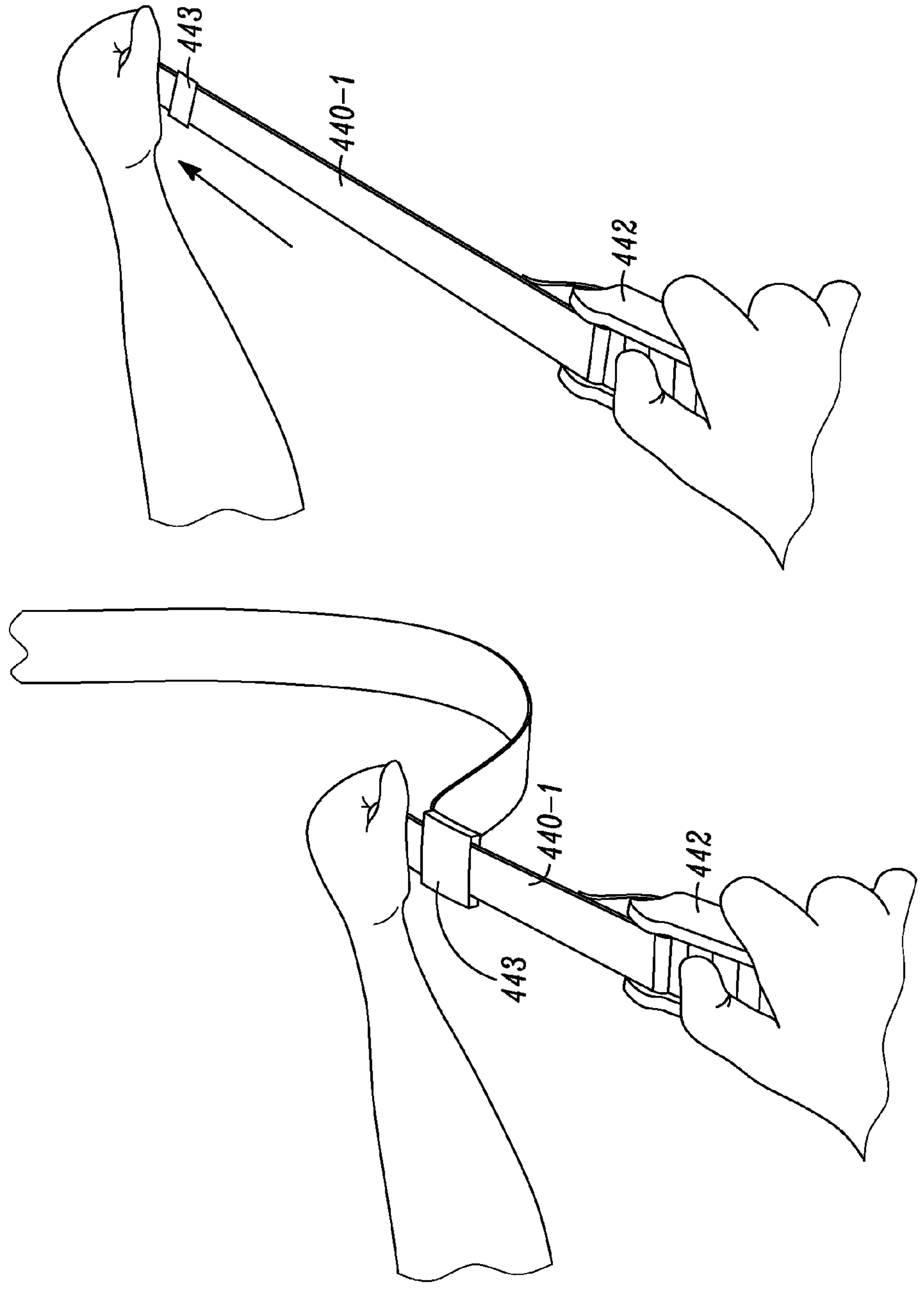
Figure 7A:
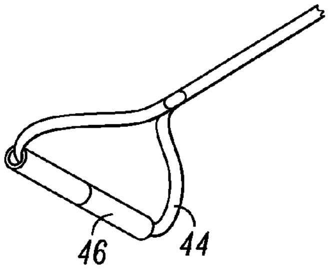
FIG. 7A-H are illustrations of various embodiments of the anchor member at one end of the anchor strap, the anchor member being in the form of a loop with grip (FIG. 7A), straight bar (FIG. 7B), curve hook (FIG. 7C), rigid or flexible curved tube or sling (FIGS. 7D, 7E & 7F) or two loops (FIGS. 7G & 7H).
Figure 7B:
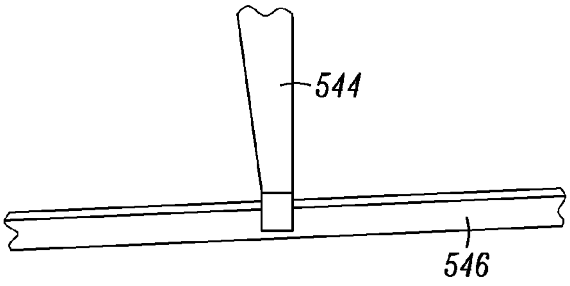
Figure 7C:
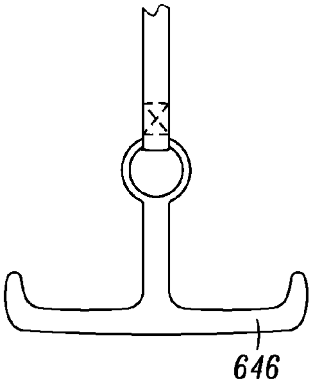
Figure 7D:
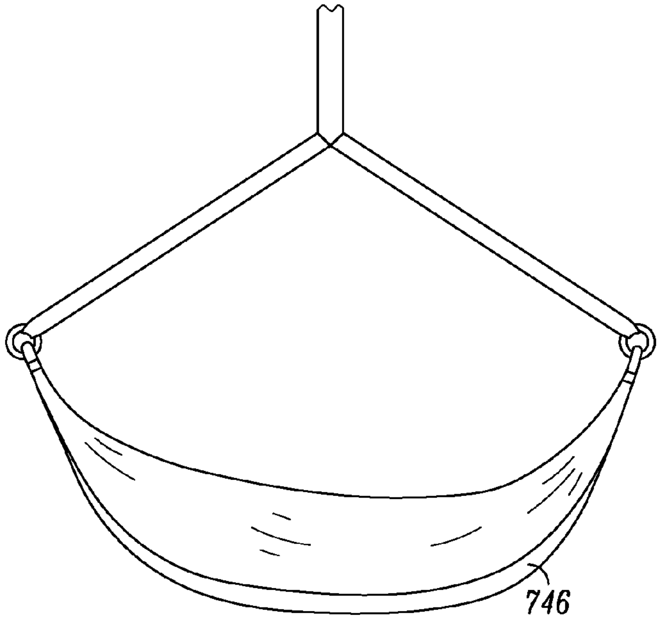
Figure 7E:
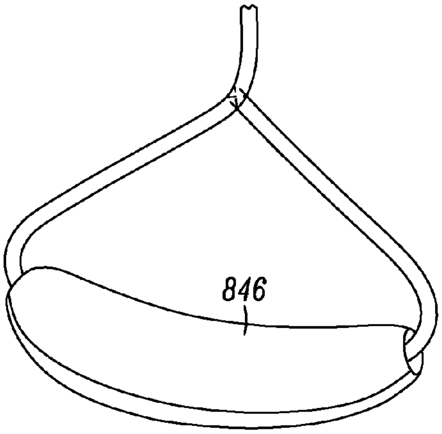
Figure 7F:
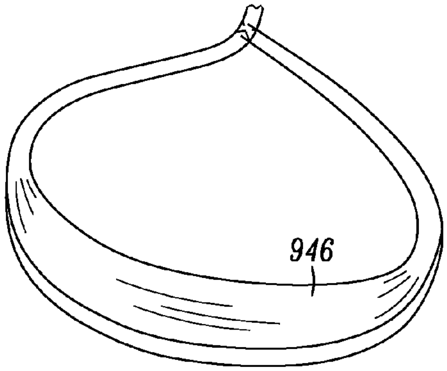
Figure 7G:
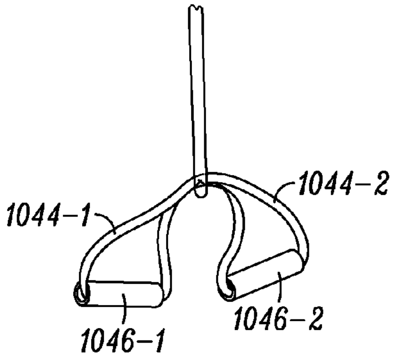
Figure 7H:
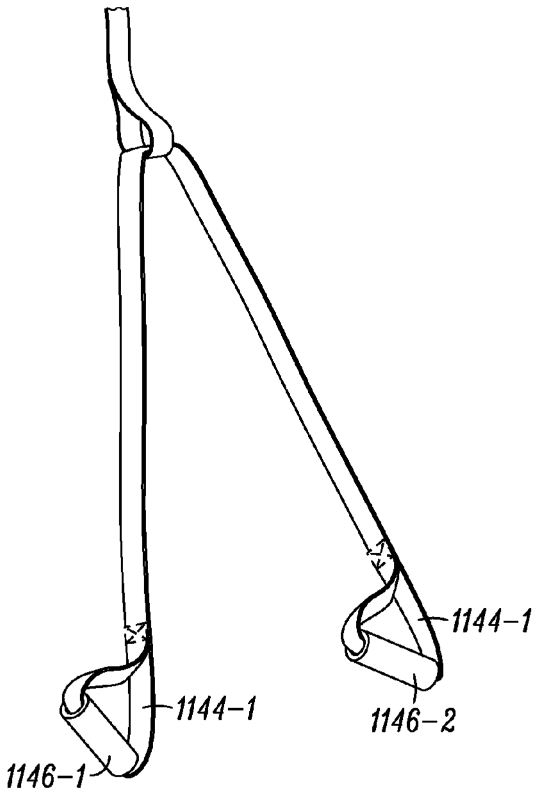

FIG. 6A shows anchor strap 440 with first segment 440-1 joined to anchor segment 440-2 by cam buckle 442. First segment 440-1 is coupled to belt at one end through square or rectangular ring 522. The other end of segment 440-1 is inserted through slot 442-1 of cam buckle 442, and then secured to the main body portion of segment 440-1 by insertion through one or more sleeves 443 (FIGS. 6A & 6B). Anchor segment 440-2 is secured to cam buckle 442 at a first end, while its second end forms anchor loop 444 (FIG. 6A). The first end of anchor segment 440-2 is inserted through slot 442-2 of cam buckle 442 (FIGS. 6A & 6B), and then stitched to the main body portion of anchor segment 440-2, while the second end is folded back on itself and stitched to a region on the main body portion at stitch 445 to form loop 444. The effective length of anchor strap 440 can be adjusted by adjusting the length of first segment 440-1. To shorten the length of the anchor strap 440, cam release button 442-3 is depressed allowing segment 440-1 to slide freely through slot 442-1. By tugging the end of 440-1 away from cam buckle 442 as shown in FIG. 6C, segment 440-1 is shortened. At the desired length, cam release button 442-3 is released holding segment 440-1 in place. Components shown in FIGS. 5 and 6 are summarized below.

| | |
|---|---|
| Ring | 522 |
| Anchor strap | 340 |
| 1st strap segment | 340-1 |
| 2nd strap segment | 340-2 |
| Quick-release buckle | 342 |
| Anchor loop | 344 |
| Anchor loop grip | 346 |
| Fixed threading plate | 343 |
| Anchor strap | 440 |
| 1st strap segment | 440-1 |
| 2nd strap segment | 440-2 |
| Cam buckle | 442 |
| 1st buckle slot | 442-1 |
| 2nd buckle slot | 442-2 |
| Cam release button | 442-3 |
| Anchor loop | 444 |
| Anchor loop grip | 446 |
| Anchor loop stitch | 445 |
| Fixed threading plate | 443 |

FIG. 7A-H illustrate various embodiments of an anchor member at the end of an anchor strap of the invention. The anchor member be in the form of loop 44 with grip 46 (FIG. 7A), a straight bar 546 (7B), a curve hook 646 (7C), a rigid or flexible curved tube or sling (7D, 7E & 7F) or two loops with grips (7G & 7H).

Figure 8A:
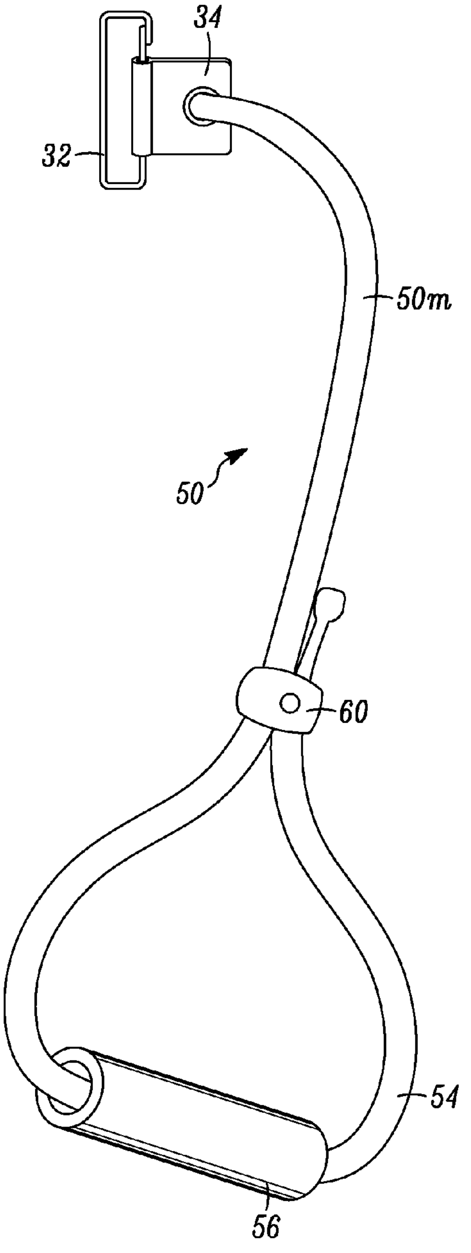
FIG. 8A-B are perspective views of a resistance member (8A) and a resistance member connector (8B).
Figure 8B:
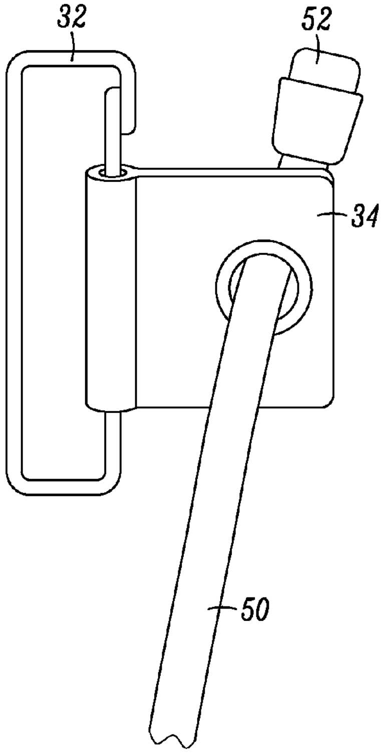

FIG. 8A illustrates an embodiment of the resistance member. Resistance member 50 is threaded through connector with reinforced eyelet 34, which is secured to belt clip 32 on one end, while the other end curves back on itself to form loop 54 held in place by spring-loaded band lock 60. The Loop 54 includes handle 56 to facilitate grip. As spring-loaded band lock 60 can be secured at many points along the length of resistance member 50, the effective length of resistance member 50 (i.e. distance from belt to free loop end), as well as size of loop 54, can be independently adjusted thereby allowing the user to establish a desired resistance level. Bulged end 52 of resistance member 50 ensures that resistance member 50 remains linked to connector 32 (FIG. 8B).

Figure 9A:
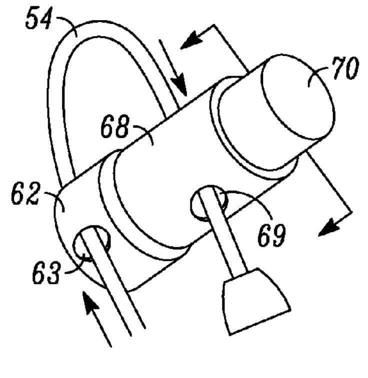
FIG. 9A-C are perspective, exploded and cross-sectional views, respectively, of a spring-loaded lock for securing an end portion of a resistance band or tubing to another portion of a resistance band or tubing to form the handle of a resistance member.
Figure 9B:
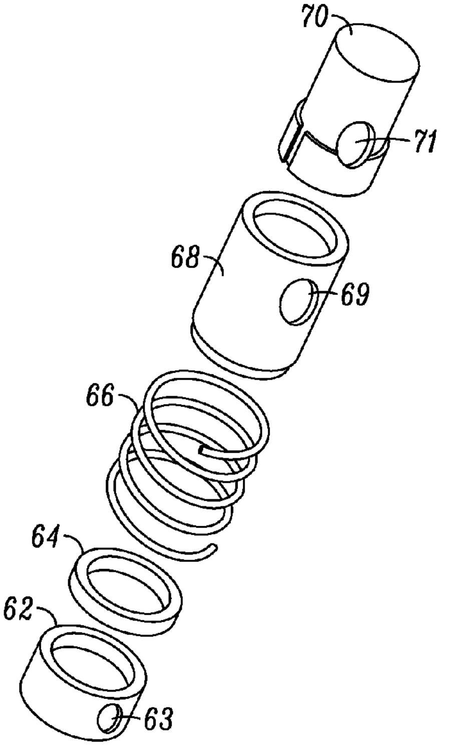
Figure 9C:
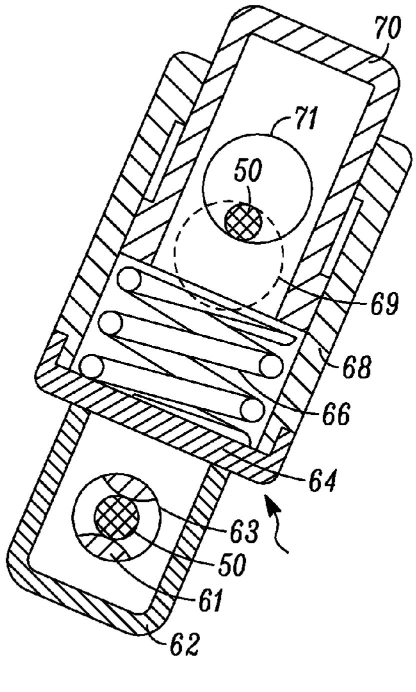

FIG. 9A provides a close-up view of loop 54 held by resistance member adjuster 60. The distal end of the resistance member enters stationary hole 63 in the direction shown by the arrow and then curves back to pass through adjustable hole 69 in the direction shown. Resistance member 50 moves freely through adjustable hole 69 when button 70 is depressed resulting in the alignment of holes 69 and 71 and allowing the length and resistance of the band or tubing to be adjusted. Stationary hole 63 is not adjustable; it is fixed onto the resistant band or tubing. The components of spring-loaded band lock 60 are shown in FIG. 9B. Stationary shell 62 is connected to outer shell 68 at one end through connective piece 64, while button case 70 inserts into the other end of outer shell 68. The shells and/or button case can be held in place by adhesive or ridges (e.g. ridges on outer side of button case 70 and inner side of outer shell 68). Spring 66 is housed in outer shell 68, held in a loaded position between stationary shell 62 and button case 70 (FIG. 9C). In this configuration, loaded spring 66 pushes button case 70 upward (or outward) maintaining it in a raised position, in which case, button hole 71 and outer shell hole 69 are offset thereby creating a narrow opening that pinches on the resistance band or tubing holding it in place. When button case 70 is pressed into outer shell 68 compressing spring 66, button hole 71 slides under outer-shell hole 69 thereby becoming aligned with out-shell hole 69 and forming a full opening through which resistance band or tubing can freely pass. Resistance band or tubing segment that passes through stationary hole 63 of stationary shell 62 is held in place by compressor 61. Components shown in FIGS. 8 and 9 are summarized below.

| | |
|---|---|
| Resistance member | 50 |
| Band loop | 54 |
| Spring-loaded band lock | 60 |
| Band lock grip | 61 |
| Stationary shell | 62 |
| Stationary shell opening | 63 |
| Shell connector | 64 |
| Band lock spring | 66 |
| Outer shell | 68 |
| Outer shell opening | 69 |
| Button case | 70 |
| Button opening | 71 |
| Band lock spring | 66 |
| Outer shell | 68 |
| Outer shell opening | 69 |

Figure 11A:
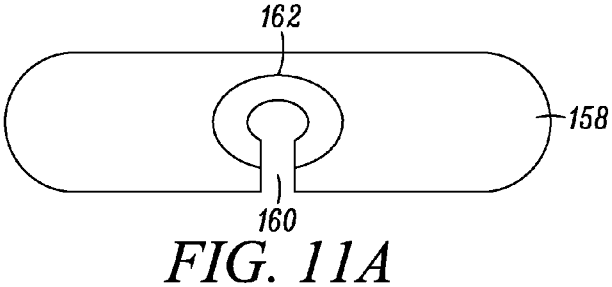
FIG. 11A-B are top and front perspective views, respectively, of the rigid handle of FIG. 10.
Figure 11B:
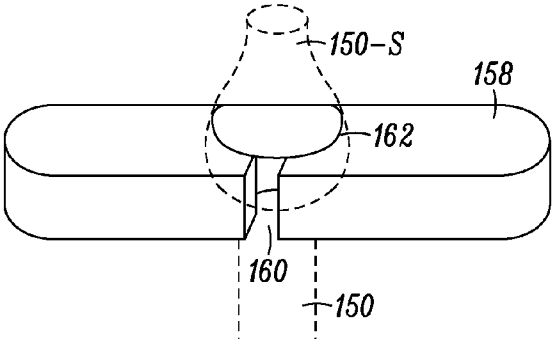

FIG. 10 illustrates a handle with which resistance bands or tubings of different lengths or tension can be used as desired by the individual user of the device. Handle 154 includes narrow passage 160 on one side of the handle through which resistance band or tubing 150 with a bulge stop 150-S can be inserted. Narrow passage 160 allows band or tubing 150 to pass through, while bulged stop 150-S rests in the cradle 162 thereby securing resistance band or tubing 150 to handle 154. Superior and perspective views of handle 154 are provided in FIGS. 11A and 11B. FIG. 11A shows the relative sizes of the opening of narrow passage 160 and cradle 162 as view directly on from the direction of grip pin 156. FIG. 11B shows narrow passage 160 extending through the entire depth of the base of handle 154 and from one side of the handle through to the center cradle 162, while cradle 162 extending through only a portion of the depth of the base.

Figure 12:
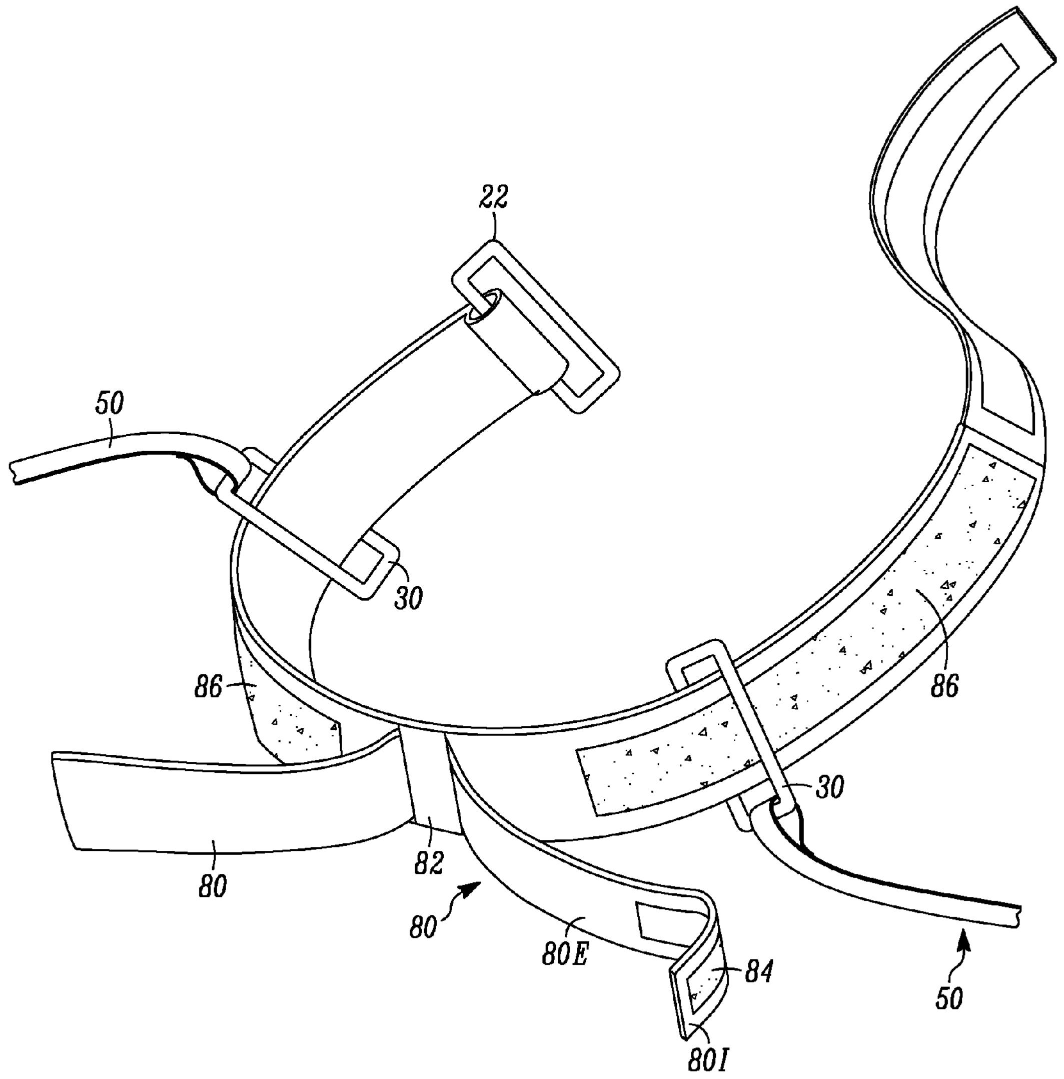
FIG. 12 is a perspective view of another embodiment of a belt that can be used in a device of the invention.

In some embodiments, the lumbar belt can include additional elastic bands at the rear or rear and side of the belt for increased stability or better fit as known to those of skill in the art (see U.S. Pat. No. 5,086,759). An example of such a belt is shown in FIG. 12. In these embodiments, elastic bands 80 are secured to center tab 82 at one end. Elastic bands 80 include, on their inner faces, strips of loop (or hook) fastener 84 that attach to strips of hook or loop fastener 86 on the exterior face of the posterior section of belt 20 on either side of center tab 82. To improve stability and fit, elastic bands 80 are stretched and secured to belt 20.

FIG. 13 illustrates detachable pouch 90 characterized by sections 90-1, 90-2 and 90-3. Detachable pouch 90 includes hook and loop fastener members 92-1 and 92-2 and pocket 94 for attaching other therapeutic devices to belt 20. Hook and loop fastener member 92-1 is attached to section 90-1 of pouch 90 on the exterior face of pouch 90. Pocket 94 is in section 90-2 of pouch 90 on the inner face. Pocket 94 is configured to receive therapeutic device 98, which can be a hot or cold pack, vibration device or acupressure ball packed with filler such as beans, rice or other dense material. Hook and loop fastener member 92-2, which is complementary to member 92-1, is attached to section 90-3 of detachable pouch 90 on its inner face, so that when the pouch is folded around belt 20 at fold lines 96-1 and 96-2, sections 90-1 and 90-3 overlap, bringing hook and loop fastener members 92-1 and 92-2 together to adhere thereby securing detachable pouch 90 containing therapeutic device 98 to belt 20. Components shown in FIG. 13 are summarized below.

| | |
|---|---|
| Elastic band attachment | 80 |
| Elastic band exterior surface | 80E |
| Elastic band interior surface | 80I |
| Elastic band connector | 82 |
| Hook & look fastener | 84 |
| Hook & loop fastener | 86 |
| Detachable pouch | 90 |
| Pouch sections | 90-1, 90-2 & 90-3 |
| Fold lines | 96-1, 96-2 & 96-3 |
| Hook & loop fastener | 92-1 |
| Hook & loop fastener | 92-2 |
| Pocket | 94 |
| Therapeutic device | 98 |

FIG. 14 illustrates engagement of a user's foot with the anchor member to assist in maintaining the lumbar belt in a desired position, as well as to apply decompression to the spine. After fastening the lumbar belt at a select position around the user's lumbar region, the user can adjust the length of the anchor strap so that the anchor member extends to a position within reach of the user's foot. Where the anchor strap terminates in a loop as shown in FIG. 14A, the user's foot can engage with the anchor member by inserting into the loop. By holding the foot in position, the anchor strap prevents movement of the lumbar belt to which it is coupled from moving upwards on the user during use. In addition, the foot engaging with the anchor member also results in a downward force that causes decompression at the spinal segment at which the lumbar belt is targeted. By plantar flexing at the angle in the direction of the arrow as shown in FIG. 14B, the user can a further apply decompression to the spine.

FIG. 15 illustrates the use of a spinal therapy device of the invention in a variety of exercise positions beneficial to the spine. Belt 20 is fastened around the user's lumbar region. Strap 40, which is coupled to belt 20, is anchored to the user's foot, while resistance members 50, also coupled to belt 20, are extended by the user in various ways. For example, the user, lying in prone engages with the anchor member using her foot thereby providing an initial decompression of the spine. Then while holding on to the handles of the resistance members, the user exerts a force through the resistance members by extending the arms above the head as shown in FIG. 15A. This creates two equal but opposite forces on the spine resulting in a directional force that is perpendicular to the spine as indicated by the arrow. The user can also exert a force through the resistance member 50 by adopting a prong on elbows position as shown in FIG. 15B or a press-up position as shown in FIG. 15C. These positions also create two equal but opposite forces on the spine resulting in a directional force that is perpendicular to the spine as indicated by the arrow. Coupled with the spinal decompression, the overpressure is more tolerable to the user. Overpressure can be applied in a supine knee-to-chest position as shown in FIG. 15D. Belt 20 is secured to the lumbar region of the user, who performs a double knee to chest exercise in a supine position with hands wrapped around the knees as shown. By gripping the handles of resistance members 50 and extending the members as the user's hands reach up to wrap the knees, the user generates a flexion overpressure force at the level of the dysfunction.

A spinal therapy device of the invention can also be used to self-apply overpressure in a standing position. FIGS. 16A and 16B illustrate use of anchor strap 40 coupled to belt 20 for standing extension exercises with overpressure to a select region of the spine. The user, with belt fastened to the lumbar region and anchor strap secured to the foot (FIG. 16A), can extend backwards over the belt as shown in FIG. 16B. By anchoring strap 40 to the user's foot, a downward pressure is exerted through strap 40 to limit any movement at a specific vertebral level, while overpressure is created at the selected spinal segment by the belt as the user extends backwards over the belt. FIGS. 17A and 17B demonstrate standing extensions to create overpressure to the spine using the resistance members. In this exercise, belt 20 is fastened to the user's lumbar region. Strap 40 is anchored to the user's foot creating a downward pressure that limits movement at the specific vertebral level. The user grips the handles of resistance members 50 holding the resistance members 50 extended away from the body as shown in FIG. 17A, thereby creating overpressure at a select spinal segment in the direction shown by the arrow. The user can increase the overpressure being applied by bending backwards over the belt and keeping the arms extended as shown in FIG. 17B. Overpressure may also be applied in a standing position without the anchor strap. In these embodiments, resistance members 50 are extended outwardly from the torso so as to direct a force perpendicular to the spine.

FIGS. 18A and 18B illustrate use of anchor strap 40 coupled to belt 20 to apply overpressure in a standing backbend exercise. Strap 40 coupled to belt 20 is anchor to a door as shown in FIG. 18A. Belt 20 is fastened around the user in a position that targets a select spinal segment. The user holds on to anchor strap 40 while bending backwards and letting gravity assist in providing overpressure to the spinal segment. FIG. 18B provides a close-up illustration of how the anchor strap 40 is secured to closed door using anchor loop 44 as a stop.

Figure 19A:
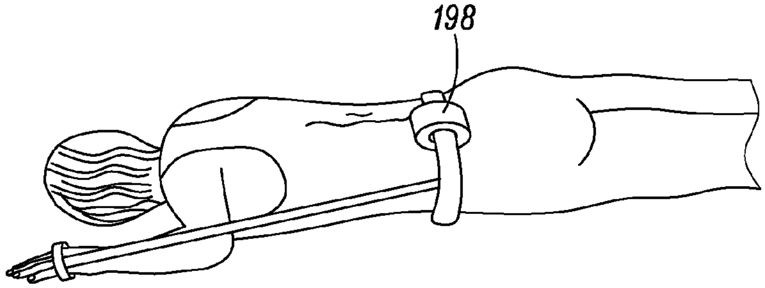
FIG. 19A-C illustrate use of a vibration device coupled to the lumbar belt for spinal joint mobilization.
Figure 19B:
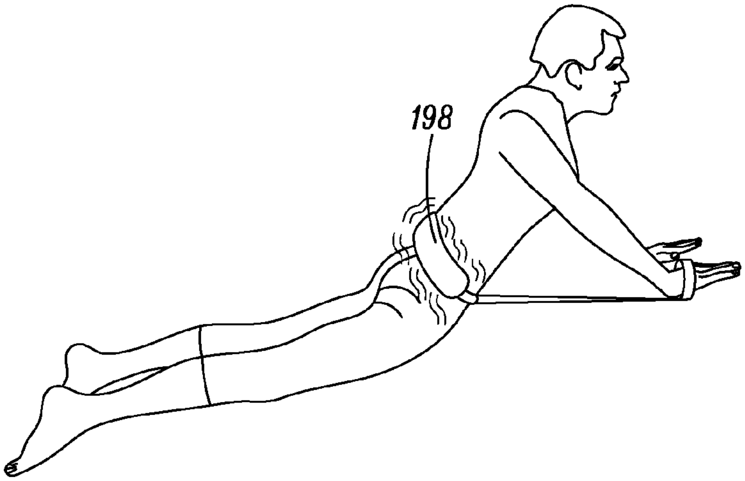
Figure 19C:
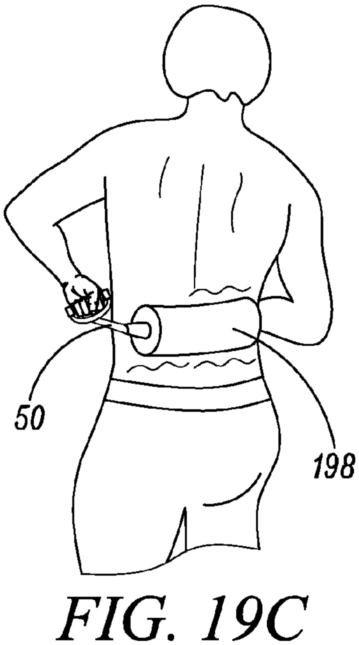

FIGS. 19A, 19B and 19C illustrate the coupling of a therapeutic vibration device 198 with the lumbar belt for spinal joint mobilization. Belt 20 is fastened around the user's lumbar region and positioned to target a select spinal segment. The coupled therapeutic device 198 generates a vibration that is transmitted to the targeted spinal segment. Joint mobilization can be achieved in various positions including, for example, as the user lies prone (19A), in a prone with press up (19B) or in standing position (19C).

Other Embodiments of the Invention

The specific methods and devices described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Under no circumstances may the patent application be interpreted to be limited to the specific examples or embodiments or methods specifically disclosed herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Although the present invention has been specifically disclosed by preferred embodiments and optional features, modification and variation of the concepts herein disclosed may be resorted to by those skilled in the art, and such modifications and variations are considered to be within the scope of this invention as defined by the appended claims. In addition, the invention has been described broadly and generically herein. Each of the narrower species and subgeneric groupings falling within the generic disclosure also form part of the invention.

What is claimed is:

1. A spinal therapy device comprising:

(a) a belt for fastening around a user's lumbar region, the belt comprising a belt fastening assembly for detachably securing the effective ends of the belt together;

(b) a length-adjustable anchor strap including a first end and a second end, the first end forming a loop and coupling to the belt through the loop, the loop maintained by securing a portion of the strap on one side of the belt to a portion of the strap on the other side of the belt by stitching, a hook and loop fastener, an adjustable slide, a fixed threading plate, or one or more snaps, the loop thereby transversely encircling the belt enabling the anchor strap to hang from the belt, the second end comprising an anchor member effective to receive a user's foot; and (c) a first and a second resistance member, each slidably coupled to the belt at one end and comprising a handle at the other end.

2. The spinal therapy device of claim 1, wherein the belt comprises leather, nylon, canvas, rubber, plastic, cotton, polyvinyl chloride, polyester or polypropylene or a combination thereof.

3. The spinal therapy device of claim 1, wherein the belt fastening assembly comprises a quick-release buckle and an adjustable slide or fixed threading plate, and wherein each end of the belt is inserted through a slot on a member of the quick-release buckle, then secured to a portion of the corresponding uninserted section by stitching, a hook and loop fastener, the adjustable slide or fixed threading plate, or one or more snaps.

4. The spinal therapy device of claim 1, wherein the resistance members are coupled to the belt through one or more connectors.

5. The spinal therapy device of claim 4, wherein the one or more connectors comprise a ring, flexible loop, clip, snap, hook, buckle or any combination thereof.

6. The spinal therapy device of claim 5, wherein the flexible loop is made of the same material as the belt.

7. The spinal therapy device of claim 4, wherein the one or more connectors comprises metal, leather, canvas, rubber, plastic, polyvinyl chloride, polypropylene, polyester or a combination thereof.

8. The spinal therapy device of claim 1, wherein the anchor member comprises a loop effective to engage a user's foot.

9. The spinal therapy device of claim 8, wherein the loop is formed by stitching the end of the anchor strap to another portion of the anchor strap thereby forming a loop having an opening effective to engage a user's foot.

10. The spinal therapy device of claim 1, wherein the handle of the resistance member is formed by securing the end portion of the resistance member to another portion to form a loop.

11. The spinal therapy device of claim 1, wherein each resistance member comprises a loop at one end that transversely encircles the belt thereby coupling the resistance member to the belt, wherein the loop is formed by securing an end portion of the resistance member to another portion.

12. A spinal therapy device comprising:

(a) a belt for fastening around a user's lumbar region, the belt comprising a belt fastening assembly for detachably securing the effective ends of the belt together;

(b) a length-adjustable anchor strap including a first end and a second end, wherein the first end is coupled to the belt, and the second end comprises an anchor member comprising a loop effective to receive a user's foot, the loop including a section encased in a rigid material; and (c) a first and a second resistance member, each slidably coupled to the belt at one end and comprising a handle at the other end.

13. The spinal therapy device of claim 12, wherein the material comprises polyurethane, plastic, rubber, ethylene vinyl acetate or a combination thereof.

14. The spinal therapy device of claim 12, wherein the anchor strap, resistance members or anchor strap and resistance members are coupled to the belt through one or more connectors.

15. The spinal therapy device of claim 14, wherein the one or more connectors comprise a ring, flexible loop, clip, snap, hook, buckle or any combination thereof.

16. The spinal therapy device of claim 14, wherein the one or more connectors comprises metal, leather, canvas, rubber, plastic, polyvinyl chloride, polypropylene, polyester or a combination thereof.

17. A spinal therapy device, comprising:

(a) a belt for fastening around a user's lumbar region, the belt comprising a belt fastening assembly for detachably securing the effective ends of the belt together;

(b) a length-adjustable anchor strap, one end coupled to the belt, the other end comprising an anchor member effective to receive a user's foot; and (c) a first and a second resistance member, each resistance member including a first end and a second end, the first end slidably coupled to the belt, the second end comprising a handle formed by securing the end portion of the second end to another portion of the resistance member to form a loop, the loop including a section encased in a rigid material to facilitate grip.

18. The spinal therapy device of claim 17, wherein the material comprises polyurethane, plastic, rubber, ethylene vinyl acetate or a combination thereof.

19. The spinal therapy device of claim 17, wherein each resistance member comprises a loop at one end that transversely encircles the belt thereby coupling the resistance member to the belt, wherein the loop is formed by securing an end portion of the resistance member to another portion.

20. The spinal therapy device of claim 17, wherein the anchor strap, resistance members or anchor strap and resistance members are coupled to the belt through one or more connectors.

* * * * *